United States Patent
de la Fuente et al.

(10) Patent No.: US 7,214,784 B2
(45) Date of Patent: *May 8, 2007

(54) **PROTECTIVE ANTIGENS FOR THE CONTROL OF *IXODES* SPECIES INFESTATIONS**

(75) Inventors: Jose de Jesús de la Fuente, Stillwater, OK (US); Katherine M. Kocan, Perkins, OK (US); Consuelo García-Almazán, Stillwater, OK (US); Jose Carlos García-García, Stillwater, OK (US); Edmour F. Blouin, Perkins, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 490 days.

This patent is subject to a terminal disclaimer.

(21) Appl. No.: 10/425,563

(22) Filed: Apr. 29, 2003

(65) Prior Publication Data

US 2004/0022795 A1 Feb. 5, 2004

Related U.S. Application Data

(60) Provisional application No. 60/376,251, filed on Apr. 29, 2002.

(51) Int. Cl.
 *C07H 21/04* (2006.01)
 *A01N 25/00* (2006.01)
(52) U.S. Cl. ..................... 536/23.5; 424/405
(58) Field of Classification Search .............. 536/23.5; 424/405
 See application file for complete search history.

(56) References Cited

U.S. PATENT DOCUMENTS

| 4,447,537 A | 5/1984 | Yunker et al. ............ 435/235 |
| 5,344,645 A | 9/1994 | Wikel ...................... 424/265.1 |
| 5,587,311 A | 12/1996 | Cobon et al. ............. 435/240.2 |
| 6,235,283 B1 | 5/2001 | Cobon et al. ............. 424/185.1 |
| 6,312,915 B1 | 11/2001 | Nelson et al. ............. 435/7.1 |

FOREIGN PATENT DOCUMENTS

| WO | WO 01/40469 | 6/2001 |
| WO | WO 01/80881 A1 | 11/2001 |
| WO | WO 03/093416 A2 | 11/2003 |

OTHER PUBLICATIONS

Result No. 3 from a search of the EST database on May 12, 2006, alignment of SEQ ID No. 3 with a polynucleotide from the tick Ornithodoros porcinus porcinus, EST database record No. CB722011, contributed by Neilan et al., "Sequence analysis of *Ornithodoros porcinus* porcinus whole tick cDNA libraries," unpublished, Apr. 10, 2003.*

(Continued)

*Primary Examiner*—Jon Weber
*Assistant Examiner*—Rosanne Kosson
(74) *Attorney, Agent, or Firm*—Fellers, Snider, Blankenship, Bailey & Tippens

(57) ABSTRACT

Protective antigens against infestations with *Ixodes* spp. ticks, gene sequences and encoded proteins for such antigens, related vaccines and methods useful to induce an immune response, which are protective to interfere with infestations by *Ixodes* spp. ticks are presented.

5 Claims, 4 Drawing Sheets

OTHER PUBLICATIONS

Alberti E, Acosta A, Sarmiento ME, Hidalgo C, Vidal T, Fachado A, Fonte L, Izquierdo L, Infante JF, Finlay CM, Sierra G. Specific cellular and humoral immune response in Balb/c mice immunised with an expression genomic library of *Trypanosoma cruzi*. Vaccine 1998; 16: 608-12.

Altschul SF, Gish W, Miller W, Myers EW, Lipman DJ. Basic local alignment search tool. J Mol Biol 1990; 215: 403-10.

Barry MA, Lai WC, Johnston SA. Protection against mycoplasma infection using expression-library immunization. Nature 1995; 377: 632-5.

Black WC 4th, Piesman J. Phylogeny of hard- and soft-tick taxa (Acari: Ixodida) based on mitochondrial 16S rDNA sequences. Proc Natl Acad Sci U S A 1994; 91: 10034-8.

Brayton KA, Vogel SW, Allsopp BA. Expression library immunization to identify protective antigens from *Cowdria ruminantium*. Ann N Y Acad Sci 1998; 849: 369-71.

Cassataro J, Velikovsky CA, Giambartolomei GH, Estein S, Bruno L, Cloeckaert A, Bowden RA, Spitz M, Fossati CA. Immunogenicity of the *Brucella melitensis* recombinant ribosome recycling factor-homologous protein and its cDNA. Vaccine 2002; 20: 1660-9.

de la Fuente J, Rodriguez M, Garcia-Garcia JC. Immunological control of ticks through vaccination with *Boophilus microplus* gut antigens. Ann N Y Acad Sci 2000; 916: 617-21.

de la Fuente J, Rodriguez M, Montero C, Redondo M, Garcia-Garcia JC, Mendez L, Serrano E, Valdes M, Enriquez A, Canales M, Ramos E, Boue O, Machado H, Lleonart R. Vaccination against ticks (*Boophilus* spp.): the experience with the Bm86-based vaccine Gavac. Genet Anal 1999; 15: 143-8.

de la Fuente J, Rodriguez M, Redondo M, Montero C, Garcia-Garcia JC, Mendez L, Serrano E, Valdes M, Enriquez A, Canales M, Ramos E, Boue O, Machado H, Lleonart R, de Armas CA, Rey S, Rodriquez JL, Artiles M, Garcia L. Field studies and cost-effectiveness analysis of vaccination with Gavac against the cattle tick *Boophilus microplus*. Vaccine 1998; 16: 366-73.

De Rose R, McKenna RV, Cobon G, Tennent J, Zakrzewski H, Gale K, Wood PR, Scheerlinck JP, Willadsen P. Bm86 antigen induces a protective immune response against *Boophilus microplus* following DNA and protein vaccination in sheep. Vet Immunol Immunopathol 1999; 71: 151-60.

de Vos S, Zeinstra L, Taoufik O, Willadsen P, Jongejan F. Evidence for the utility of the Bm86 antigen from *Boophilus microplus* in vaccination against other tick species. Exp Appl Acarol 2001; 25: 245-61.

Drew DR, Lightowlers M, Strugnell RA. Vaccination with plasmid DNA expressing antigen from genomic or cDNA gene forms induces equivalent humoral immune responses. Vaccine 1999; 18: 692-702.

Elad D, Segal E. Immunogenicity in calves of a crude ribosomal fraction of *Trichophyton verrucosum*: a field trial. Vaccine 1995; 13: 83-7.

Estrada-Peña A, Jongejan F. Ticks feeding on humans: a review of records on human-biting Ixodoidea with special reference to pathogen transmission. Exp Appl Acarol 1999; 23: 685-715.

Garcia-Garcia JC, Gonzalez IL, Gonzalez DM, Valdes M, Mendez L, Lamberti J, D'Agostino B, Citroni D, Fragoso H, Ortiz M, Rodriguez M, de la Fuente J. Sequence variations in the *Boophilus microplus* Bm86 locus and implications for immunoprotection in cattle vaccinated with this antigen. Exp Appl Acarol 1999; 23: 883-95.

Kofta W, Wedrychowicz H. c-DNA vaccination against parasitic infections: advantages and disadvantages. Vet Parasitol 2001; 100: 3-12.

Liyou N, Hamilton S, Elvin C, Willadsen P. Cloning and expression of ecto 5'-nucleotidase from the cattle tick *Boophilus microplus*. Insect Mol Biol 1999; 8: 257-66.

Liyou N, Hamilton S, Mckenna R, Elvin C, Willadsen P. Localization and functional studies on the 5'-nucleotidase of the cattle tick *Boophilus microplus*. Exp Appl Acarol 2000; 24: 235-46.

Manoutcharian K, Terrazas LI, Gevorkian G, Govezensky T. Protection against murine cysticercosis using cDNA expression library immunization. Immunol Lett 1998; 62; 131-6.

Melby PC, Ogden GB, Flores HA, Zhao W, Geldmacher C, Biediger NM, Ahuja SK, Uranga J, Melendez M. Identification of vaccine candidates for experimental visceral leishmaniasis by immunization with sequential fractions of a cDNA expression library. Infect Immun 2000; 68: 5595-602.

Moore RJ, Lenghaus C, Sheedy SA, Doran TJ. Improved vectors for expression library immunization—application to *Mycoplasma hyopneumoniae* infection in pigs. Vaccine 2001; 20: 115-20.

Mulenga A, Sugimoto C, Onuma M. Issues in tick vaccine development: identification and characterization of potential candidate vaccine antigens. Microbes Infect 2000; 2: 1353-61.

Munderloh UG, Wang YLM, Chen C, Kurtti TJ. Establishment, maintenance and description of cell lines from the tick *Ixodes scapularis*. J Parasitol 1994; 80: 533-43.

Nuttall PA. Pathogen-tick-host interactions: *Borrelia burgdorferi* and TBE virus. Zentralbl Bakteriol 1999; 289: 492-505.

Parola P, Raoult D. Tick-borne bacteriol diseases emerging in Europe. Clin Microbiol Infect 2001; 7: 80-3.

Silva CL. The potential use of heat-shock proteins to vaccinate against mycobacterial infections. Microbes and Infection 1999; 1: 429-35.

Singh RA, Wu L, Barry MA. Generation of genome-wide CD8 T cell responses in HLA-A*0201 transgenic mice by an HIV-1 ubiquitin expression library immunization vaccine. J Immunol 2002; 168: 379-91.

Smooker PM, Setiady YY, Rainczuk A, Spithill TW. Expression library immunization protects mice against a challenge with virulent rodent malaria. Vaccine 2000; 18: 2533-40.

van Drunen Littel-van den Hurk S, Loehr BI, Babiuk LA. Immunization of livestock with DNA vaccines; current studies and future prospects. Vaccine 2001; 19: 2474-9.

Wikel SK, Ramachandra RN, Bergman DK, Burkot TR, Piesman J. Infestation with pathogen-free nymphs of the tick *Ixodes scapularis* induces host resistance to transmission of *Borrelia burgdorferi* by ticks. Infect Immun 1997; 65: 335-8. Willadsen P. Novel vaccines for ectoparasites. Vet Parasitol 1997; 71: 209-22.

Willadsen P, Jongejan F. Immunology of the tick-host interaction and the control of ticks and tick-borne diseases. Parasitol Today 1999; 15: 258-62.

Alamzán, C., Kocan, K.M., Bergman, D.K., Garcia-Garcia, J.C., Blouin, E.F., de la Fuente, J., "Identification of protective antigens for the control of *Ixodes scapularis* infestations using cDNA expression library immunization", *Vaccine* 2003; 21: 1492-1501.

De La Fuente, J., Kocan, K.M., "Advances in the identification and characterization of protective antigens for recombinant vaccines against tick infestations", *Expert Rev. Vaccines* 2003; 2(4): 583-593.

Alamzán, C., Kocan, K.M., Bergman, D.K., Garcia-Garcia, J.C., Blouin, E.F., de la Fuente, J., "Characterization of genes transcribed in an *Ixodes scapularis* cell line that were identified by expression library immunization and analysis of expressed sequence tags", *Gene Therapy Molecular Biology*, 2003, vol. 7: 43-59.

Alamazan, et al.; Characterization of three Ixodes scapularis cDNAs protective against tick infestations; Vaccine, Butterworth Scientific. Guildford, GB, vol. 23, No. 35, Aug. 15, 2005, pp. 4403-4416.

Almazan, et al.; "Vaccination with recombinant tick antigens for the control of *Ixodes scapularis* adult infestations"; Vaccine, Butterworth Scientific. Guildford, GB, vol. 23, No. 46-47; Nov. 16, 2005, pp. 5294-5298.

Search report issued by the European Patent Office in Application No. 05256580.1; Applicant: The Board of Regents of Oklahoma State University, Mar. 22, 2006.

PCT International Search Report for PCT/US03/13229, Feb. 11, 2005.

Das et al., "Salp25D, an Ixodes scapularis Antioxidant, Is 1 of 14 Immunodominant Antigens in Engorged Tick Salivary Glands," published Sep. 28, 2001, *The Journal of Infectious Diseases 2001*; 184:1056-64.

Almazan et al., "Identification of protective antigens for the control of Ixodes scapularis infestations using cDNA expression library immunization," *Vaccine*, Butlerworth Scientific, Guidford, GB, vol. 21, No. 13-14, Mar. 28, 2003, pp. 1492-1501.

Almazan et al., "Characterisation of genes transcribed in a Ixodes scapularis cell line that were identified by expression library immunization and analysis of expressed sequence tags," *Gene Therapy and Molecular Biology*, vol. 7. Jun. 2003, pp. 43-59.

* cited by examiner

SEQUENCE LISTING

<160> NUMBER OF SEQ ID NOS: 25

<210> SEQ ID NO 1
<211> LENGTH: 349
<212> TYPE: DNA
<213> ORGANISM: Ixodes scapularis

<400> SEQUENCE: 1

```
atggaaatat ctgtgaaacc aaggcccaca aaaaggaaaa gaaaggccat catcatcatg      60
gcaagaatga gaacagcatt ccccaccaga agtgggaaca gcttctcaag gacttgaaca     120
gttaatgatg tgttgtgcaa ttcgaatgtg gctgcaacct cgctagagaa catagtcgac     180
cagctgtagt gctctagtat taaccaagaa gcagtattct gccgtcatat gtacaggcag     240
atttgttacg gcattttcag cttttttta tacaaaatgt agttcttgtt taaaaaaaac     300
ctaaaataaa acaaagccac aaaaaaaaaa aaaaaaaaaa aaaaaaaaa                349
```

<210> SEQ ID NO 2
<211> LENGTH: 38
<212> TYPE: PRT
<213> ORGANISM: Ixodes scapularis

<400> SEQUENCE: 2

```
Met Glu Ile Ser Val Lys Pro Arg Pro Thr Lys Arg Lys Arg Lys Ala
1               5                   10                  15
```

```
Ile Ile Ile Met Ala Arg Met Arg Thr Ala Phe Pro Thr Arg Ser Gly
        20                  25                  30

Asn Ser Phe Ser Arg Thr
        35

<210> SEQ ID NO 3
<211> LENGTH: 2693
<212> TYPE: DNA
<213> ORGANISM: Ixodes scapularis
<220> FEATURE:
<221> NAME/KEY: misc_feature
<222> LOCATION: (685)..(685)
<223> OTHER INFORMATION: n is a, c, g, or t
<220> FEATURE:
<221> NAME/KEY: misc_feature
<222> LOCATION: (1962)..(1962)
<223> OTHER INFORMATION: n is a, c, g, or t

<400> SEQUENCE: 3
ggtttgtgct gcttggaaaa tccaccagga gcctgcaacc gcaaaaaagt tcatcatccg      60
gagctaagcc tatcgcagga tggcttgcgc aacattaaag cgaacacacg attgggatcc     120
gctgcatagt ccaaacggaa gatcgcccaa acgacggaga tgtatgcctt tgtcggtcac     180
acaagcagcg actcccccaa caagggcaca ccaaatcaac ccttcaccct tcggtgaagt     240
gccaccgaaa ttaacttcag aggagatagc ggccaacatt cgggaggaaa tgcgacgtct     300
gcagcggcgc aagcagctct gcttctcgtc tcccctggag tcgggctccc cgtcggcgac     360 tcccctgcg gccgattgcg gaccagcctc ccccacgggc ctgtccccg ggggcctgct      420 gtcgcccgtg cgcagggacc aacccctctt caccttccgc caggtggggc tcatctgcga     480
gcgcatgatg aaggagcgcg agagccagat acgcgacgag tacgaccacg ttctgtctgc     540
caagctggca gagcagtacg acacatttgt caagtttacg tacgaccaaa ttcagaagcg     600
gtttgagggt gccactccaa gctatttgtc ataacatgat gggcatctgc aaacaagcaa     660
ggaactttga gggtttgtgc tagangaag aaacccatgg tggggaagga cacaagacca     720
acacttagac tcggcaagca agccagatcc tgtggggtgc ggggacgggg ggaatgagtc     780
cagtggtgtc ttcggagttt ttttttttcc ttctcccttt ccctcgtctt cttttggca      840 caactcttta cggaactggt gtgcatccat tccccgaaag tgcaagagaa ggactcgcgg     900
cggatcatct acggaggaag aagtgtgtat gcctttgtgc tttgggtctc ctttttttt     960 ttttaaccg tcttgccatc tcgccataga agacctgtga tctagcaaac aaaggtgtgc    1020
gaatgttatg caaaggttgg aagtcagttt gaaagtggag cgagagaaaa ttttgtatgc    1080
tgagtatggt tagtcaccgt ttacttttca ggagggggat gactgaggaa cggagccgcc    1140
ccaactctcg tttgtctttt attttagga tactttctct gtggcgagaa tttgtgtgtg    1200
catgcaagtt agcgagggta cgaggaaaag aagggttata aaatattctg ggtgagagct    1260
gtagttcaac tgggggtgg gattgtaaag acctgcgggt accagagga ccgcatgctc     1320 tggctatatt acttgcattg aggggagga ggaatgctgg acctcgagca gagccagcaa    1380
gtattttgga aaggaataaa acaaaaatt ggcttagtgt acagatgtat aatatatatg    1440
cactacaggg tgtgtgtgcc tcttgtatct tcccgtgcgt tgtgtccctc ttgcggcttg    1500
cccatctgac aaccgcctgt gtacataggc aacgcaagt cttcagcatg gcaccctctt    1560
ctttttcctt tttttttct cataagtaat tttgaaggag agaatatttt gatttctaag    1620
actcccaaaa catcaagtgc tctggtggtc ggaattctac aagtgcgaaa gttccttcct    1680
tttttttgtt tcgagatagg aatggcttca ggttgtgctg cctatgcttt ggccacactt    1740
```

-continued

```
tggaacacct gcaacagcga attaactggt gtaggcctgt gacacttgca cagccgtgtt    1800
tttttttttt tttttttgtag ttttgcagta ataaaaactt gttatggaaa gagtgcatta   1860
tgctatggca ttgtctgctg ctatgcttat tggaatgcat gcctgatgtg tgttgtgctt    1920
gaggatagtg aagtggtatt gcagggttgg aaaggagctt anaatgcctt ctggcttttg    1980
cataagcgtg gctttgggtg tcgtctgagc ttgtcaatca cagtgcaaca tgcactttgt    2040
ccaattggtt tattggggac tgcttttggg tgcagagttt gactaatttt tagtaatgct    2100
tcaaatgcaa cgcttctgtg ttgatcgcag ttcatcaact cgtcgatcat tatgcatgtg    2160
aaaaactgct cacgtaaact gtatgttgat atcacagttg cactgaggaa gcctggctta    2220
agatggtgtg tgcaagtgct tggcacactg cgtattttcc agcataaagc tggtagtgta    2280
caggtgctgc tgttagtagc aaactttctg ccattgctgc cacaattcat gcatgaatga    2340
gtgttgggga gtatgttagt ttatcttttc aaaactgatt tgaagtacca gtgtcctata    2400
tttttgccat tgcattaata tggatcctgc attgtttacg gaaaaagtg ataacattaa     2460 ttatgaaaga tattaagcga gtttattgac ttttccagga gaatttagac caggaggcac    2520
tacatagcct gtggtctgct ttgttatgtt gacttggttt ttgtggaaat tagttctaaa    2580
agtttacaat cttttttggca tgacttgttt gcattgccat tgtaatttgg ccattattag   2640
aataaaggca ctctctcagt acctaaaaaa aaaaaaaaaa aaaaaaaaaa aaa           2693
```

<210> SEQ ID NO 4
<211> LENGTH: 184
<212> TYPE: PRT
<213> ORGANISM: Ixodes scapularis

<400> SEQUENCE: 4

```
Met Ala Cys Ala Thr Leu Lys Arg Thr His Asp Trp Asp Pro Leu His
1               5                   10                  15

Ser Pro Asn Gly Arg Ser Pro Lys Arg Arg Cys Met Pro Leu Ser
            20                  25                  30

Val Thr Gln Ala Ala Thr Pro Pro Thr Arg Ala His Gln Ile Asn Pro
        35                  40                  45

Ser Pro Phe Gly Glu Val Pro Pro Lys Leu Thr Ser Glu Glu Ile Ala
    50                  55                  60

Ala Asn Ile Arg Glu Glu Met Arg Arg Leu Gln Arg Arg Lys Gln Leu
65                  70                  75                  80

Cys Phe Ser Ser Pro Leu Glu Ser Gly Ser Pro Ser Ala Thr Pro Pro
                85                  90                  95

Ala Ala Asp Cys Gly Pro Ala Ser Pro Thr Gly Leu Ser Pro Gly Gly
            100                 105                 110

Leu Leu Ser Pro Val Arg Arg Asp Gln Pro Leu Phe Thr Phe Arg Gln
        115                 120                 125

Val Gly Leu Ile Cys Glu Arg Met Met Lys Glu Arg Glu Ser Gln Ile
    130                 135                 140

Arg Asp Glu Tyr Asp His Val Leu Ser Ala Lys Leu Ala Glu Gln Tyr
145                 150                 155                 160

Asp Thr Phe Val Lys Phe Thr Tyr Asp Gln Ile Gln Lys Arg Phe Glu
                165                 170                 175

Gly Ala Thr Pro Ser Tyr Leu Ser
            180
```

<210> SEQ ID NO 5

-continued

```
<211> LENGTH: 1821
<212> TYPE: DNA
<213> ORGANISM: Ixodes scapularis
<220> FEATURE:
<221> NAME/KEY: misc_feature
<222> LOCATION: (1487)..(1487)
<223> OTHER INFORMATION: n is a, c, g, or t
<220> FEATURE:
<221> NAME/KEY: misc_feature
<222> LOCATION: (1595)..(1595)
<223> OTHER INFORMATION: n is a, c, g, or t
<220> FEATURE:
<221> NAME/KEY: misc_feature
<222> LOCATION: (1606)..(1606)
<223> OTHER INFORMATION: n is a, c, g, or t
<220> FEATURE:
<221> NAME/KEY: misc_feature
<222> LOCATION: (1623)..(1623)
<223> OTHER INFORMATION: n is a, c, g, or t
<220> FEATURE:
<221> NAME/KEY: misc_feature
<222> LOCATION: (1762)..(1762)
<223> OTHER INFORMATION: n is a, c, g, or t
<220> FEATURE:
<221> NAME/KEY: misc_feature
<222> LOCATION: (1789)..(1789)
<223> OTHER INFORMATION: n is a, c, g, or t

<400> SEQUENCE: 5
atggcgtcgt gtggagcatc agcgacgggt cctctcgtcc taagagtaat ttccaacact     60
gttaaaatag ttaacagcgc cggaaagata atcaaggaca tcatgaacag tggaaacctc    120
ggaatcgtcg aaaaggaagg catcaatgac ctgcaaacgg aggcagacag atctgttcag    180
cgctgcattg tgacttcgct ctcgagacag ttcccaaaac tgacaataat tggtgaagag    240
actctggagg agaaaaagat cagcgacgac tggatcatca ccgagcatga caaggatgtc    300
ctggccactt ctctgccgga caacctgaag aacatcaaag aggaagattt ggtagtctgg    360
gttgatcctc tggatggaac caaggagtac acacagggtt tcctggacca cgtgacgatc    420
ctggtgggga ttgcggttga cggtaaggca gtgggtggag tgatccacca gccgtactac    480
aactaccagg tggagaagga cgtctacaag caggacgta ccatgtgggg cattgtcggc    540
gtcggtgcct ttgggatctc gcgcattgcg cctccggaga caagaggat catcactacg    600 acgcgctccc attccagccc caccatcaac agctgcattg aagccatgaa tccggacgag    660
gtgctgcgag ttggaggtgc cgggcacaag gtgctgctgt tgattgaggg caaggctcac    720
gcttacgtgt ttcccagcaa agggtgcaag aaatgggaca cttgtgcccc cgaagcgatt    780
cttcatgcca ctggcggcct tcttacagat gttcacggga acagattgga gtaccacaag    840
gacgtggaac acgtcaatgc cggcggcgtt cttgccacct gcctgaagga acaaacgaa    900 tggttcaaga accacattcc cgaagatgtc cgcaagacgc ttcctctatg agcaacctgc    960
cgttgtccgt tgcgatcaca ctcaagtcgc gttttcctt taactttgtg gtgatgcggt   1020
tcaaagtctt atactattag tgttttggtg gtccaaatat tattactaaa aaacccgga   1080 gacatgggac acaaaaaaat ggaggggcgg gacaataagg tctcgaacac agctcgtaca   1140
gaatttttta aataatgtt gatttcaggt ttatttgtgg aaactctgaa attaaccgtt   1200
atgtcattat ttgggttgtg ccgtttgaaa ttttatgaaa tacgtaatag ctgcacgcat   1260
tttgcaggcc actcagctcc ttgaatgctc gatgcttgat gcttctgcca acattatttg   1320
tatctcaagt ttttctacca caagaaacag taccctaaca ttttgaaata gtattactag   1380
cttggatttt atctggtatg catatataag atctatggat gttcctaagg agggcatgaa   1440
tttgaaacat accctgtcct taccaacctt caaacatttt tttttgngcc tgcttaaaag   1500
```

```
cacttacatt gcttgatcgt tgaattaatt ttttagctga tgttaaggac acttataata    1560
attaaggaaa tgagatcgat cttgagcttg tttgngcctc tgtaanaatt gatgctcttt    1620
canacctaat gcttaatgca acaataatta tcaagtaatc cttactcagg tgtcagatat    1680
gcaagcagat gccaatgctt ctgttcattg agtggcaaaa ggcattgctc tttgtcacat    1740
tgcatgcatt tatgacagcc cnccttaata aactataatg cagctaatnt gaaaaaaaaa    1800
aaaaaaaaaa aaaaaaaaa a                                               1821
```

<210> SEQ ID NO 6
<211> LENGTH: 316
<212> TYPE: PRT
<213> ORGANISM: Ixodes scapularis

<400> SEQUENCE: 6

```
Met Ala Ser Cys Gly Ala Ser Ala Thr Gly Pro Leu Val Leu Arg Val
1               5                   10                  15

Ile Ser Asn Thr Val Lys Ile Val Asn Ser Ala Gly Lys Ile Ile Lys
            20                  25                  30

Asp Ile Met Asn Ser Gly Asn Leu Gly Ile Val Glu Lys Glu Gly Ile
        35                  40                  45

Asn Asp Leu Gln Thr Glu Ala Asp Arg Ser Val Gln Arg Cys Ile Val
    50                  55                  60

Thr Ser Leu Ser Arg Gln Phe Pro Lys Leu Thr Ile Ile Gly Glu Glu
65                  70                  75                  80

Thr Leu Glu Glu Lys Lys Ile Ser Asp Asp Trp Ile Ile Thr Glu His
                85                  90                  95

Asp Lys Asp Val Leu Ala Thr Ser Leu Pro Asp Asn Leu Lys Asn Ile
            100                 105                 110

Lys Glu Glu Asp Leu Val Val Trp Val Asp Pro Leu Asp Gly Thr Lys
        115                 120                 125

Glu Tyr Thr Gln Gly Phe Leu Asp His Val Thr Ile Leu Val Gly Ile
    130                 135                 140

Ala Val Asp Gly Lys Ala Val Gly Gly Val Ile His Gln Pro Tyr Tyr
145                 150                 155                 160

Asn Tyr Gln Val Glu Lys Asp Val Tyr Lys Gln Gly Arg Thr Met Trp
                165                 170                 175

Gly Ile Val Gly Val Gly Ala Phe Gly Ile Ser Arg Ile Ala Pro Pro
            180                 185                 190

Glu Asn Lys Arg Ile Ile Thr Thr Thr Arg Ser His Ser Ser Pro Thr
        195                 200                 205

Ile Asn Ser Cys Ile Glu Ala Met Asn Pro Asp Glu Val Leu Arg Val
    210                 215                 220

Gly Gly Ala Gly His Lys Val Leu Leu Leu Ile Glu Gly Lys Ala His
225                 230                 235                 240

Ala Tyr Val Phe Pro Ser Lys Gly Cys Lys Lys Trp Asp Thr Cys Ala
                245                 250                 255

Pro Glu Ala Ile Leu His Ala Thr Gly Leu Leu Thr Asp Val His
            260                 265                 270

Gly Asn Arg Leu Glu Tyr His Lys Asp Val Glu His Val Asn Ala Gly
        275                 280                 285

Gly Val Leu Ala Thr Cys Leu Lys Glu Gln His Glu Trp Phe Lys Asn
    290                 295                 300

His Ile Pro Glu Asp Val Arg Lys Thr Leu Pro Leu
```

```
                305          310          315

<210> SEQ ID NO 7
<211> LENGTH: 697
<212> TYPE: DNA
<213> ORGANISM: Ixodes scapularis
<220> FEATURE:
<221> NAME/KEY: misc_feature
<222> LOCATION: (573)..(573)
<223> OTHER INFORMATION: n is a, c, g, or t

<400> SEQUENCE: 7
gacctcaagg aaggcatctg cccgcaggcc ttctggctca acaaggagca gtgttgctgg      60
gcctccaacg ataccttctt taaggggggac gactgcaagc agtggtatcg gtggcccgag    120
atgttcgaca gcggcatgga caaggacggg gcaggctttt acctgctctc ctacctgctg    180
tacgtcatgt ggagtgtgct cttcgccacc ctggccgtca tgctcgttcg caccttcgcg    240
ccctatgcct gtggatctgg aatcccggag atcaagacga ttctgagcgg cttcatcatc    300
cgcggctacc tgggcaagtg gacgctgacc atcaaatcag tgtgtctggt gctggccgtc    360
ggggcgggcc tcagcctggg caaagagggg ccctggtgc acgtggcctg ctgcatcggg     420
aacatcttct cctacctctt ccccaagtac ggcaagaatg aggccaagaa gagggagatc    480
ctgtcggctg ccgccgccgc gggagtttct gtggcctttg ggctcccat cggcggtgtt     540 ctcttcagcc tcgaagaggt gagctactac ttnccctga agacgctgtg gcgttccttc     600
ttctgcgccc tggtggcagc ctcggtgctg cgctccatca ccccctttgg caacgaccac    660
ctggtgatgt tctacgtcga gtacgacttt ccctggc                              697

<210> SEQ ID NO 8
<211> LENGTH: 232
<212> TYPE: PRT
<213> ORGANISM: Ixodes scapularis
<220> FEATURE:
<221> NAME/KEY: misc_feature
<222> LOCATION: (191)..(191)
<223> OTHER INFORMATION: Xaa can be any naturally occurring amino acid

<400> SEQUENCE: 8

Asp Leu Lys Glu Gly Ile Cys Pro Gln Ala Phe Trp Leu Asn Lys Glu
1               5                   10                  15

Gln Cys Cys Trp Ala Ser Asn Asp Thr Phe Phe Lys Gly Asp Asp Cys
            20                  25                  30

Lys Gln Trp Tyr Arg Trp Pro Glu Met Phe Asp Ser Gly Met Asp Lys
        35                  40                  45

Asp Gly Ala Gly Phe Tyr Leu Leu Ser Tyr Leu Leu Tyr Val Met Trp
    50                  55                  60

Ser Val Leu Phe Ala Thr Leu Ala Val Met Leu Val Arg Thr Phe Ala
65                  70                  75                  80

Pro Tyr Ala Cys Gly Ser Gly Ile Pro Glu Ile Lys Thr Ile Leu Ser
                85                  90                  95

Gly Phe Ile Ile Arg Gly Tyr Leu Gly Lys Trp Thr Leu Thr Ile Lys
            100                 105                 110

Ser Val Cys Leu Val Leu Ala Val Gly Ala Gly Leu Ser Leu Gly Lys
        115                 120                 125

Glu Gly Pro Leu Val His Val Ala Cys Cys Ile Gly Asn Ile Phe Ser
    130                 135                 140

Tyr Leu Phe Pro Lys Tyr Gly Lys Asn Glu Ala Lys Lys Arg Glu Ile
145                 150                 155                 160
```

-continued

```
Leu Ser Ala Ala Ala Ala Gly Val Ser Val Ala Phe Gly Ala Pro
            165                 170                 175

Ile Gly Gly Val Leu Phe Ser Leu Glu Glu Val Ser Tyr Tyr Xaa Pro
            180                 185                 190

Leu Lys Thr Leu Trp Arg Ser Phe Phe Cys Ala Leu Val Ala Ala Ser
        195                 200                 205

Val Leu Arg Ser Ile Asn Pro Phe Gly Asn Asp His Leu Val Met Phe
    210                 215                 220

Tyr Val Glu Tyr Asp Phe Pro Trp
225                 230

<210> SEQ ID NO 9
<211> LENGTH: 1221
<212> TYPE: DNA
<213> ORGANISM: Ixodes scapularis
<220> FEATURE:
<221> NAME/KEY: misc_feature
<222> LOCATION: (713)..(713)
<223> OTHER INFORMATION: n is a, c, g, or t

<400> SEQUENCE: 9
gtttcttgtt acggtagtgg agtgctgagt ttactcgata atatctgaga aatagtggca      60
atatcaattt ttctgtaaat tagaaatgta accaatggcg tggctatctt ctagtcgaca     120
ctaacgtctc ggatctgctg ttcaaagtcc cgggcgatca agccgtattt gttgtccagc     180
tgccaagtgc gtcgaatatg atgccgaaaa agaaagaatc agtcgcgagc tctaaagaag     240
acgcgccgat cgacgtgatc ggcctgccct cccacaaacg acacaagaag cacaagcaca     300
aaaagcacaa gcgcaagcga ggcacggacc aagacgaaga ccaatcgccc gccgcgagcc     360
cgcagagcgg tggcgagggt agcagcagca agcccgcgct caagctcaag atcaagatcg     420
gcggacagac ggtcgagaag aacgtgacca agctgaaaca gcagcggccg ccgccgccgg     480
accctagcga agccgatctc gccgaactcc tgatgaaacc caactcgggc gatacgagcg     540
cagacagcga tgacgaagag gaagcctggc tcgaagccct cgagtccggc aggctcgaag     600
aggtcgacga cgagctccgc aaaatgaagg acccgaccct gatgacggcc aggcagcggg     660
ccctgctcga gagcaagtcg cagaaggacg aggtcccggc gacggggatg gcngcgtcc     720
gcggagcccg tcaaagagat gtccgaggag atgattcagc ggcggatgct gcgggccaaa     780
aagcggaagc agcaggccga agagaagaaa gagaaggaga agaagcagac gatcgagcgt     840
ctgctcaaga agtccgactc gaggctgagg gccagcaaga agttggccaa gaagagcgat     900
actcccaagg tgtcgctggt caacacgcag gcaggcacgc tgctctcgtt tcccgtcggc     960
gttgcgttcc cgctgtcggc agccgtggcc caggggtacc ccgagaagac gacgtgcggc    1020
attaagggtt gtcgtaaccc gaagaagtac tcgtgctcca agacaggcgt gccccctgtgc    1080
agcctcgagt gctacaagac gaacatgctg cagatgtgcg tctgagcggg cagctaggct    1140
tccgggctac agctgctcct tgtgtatatg tatataaagt cgagaatgct gaaaaaaaaa    1200
aaaaaaaaaa aaaaaaaaaa a                                              1221

<210> SEQ ID NO 10
<211> LENGTH: 275
<212> TYPE: PRT
<213> ORGANISM: Ixodes scapularis

<400> SEQUENCE: 10

Met Met Pro Lys Lys Lys Glu Ser Val Ala Ser Ser Lys Glu Asp Ala
```

-continued

```
                1               5              10              15
        Pro Ile Asp Val Ile Gly Leu Pro Ser His Lys Arg His Lys Lys His
                       20                  25                  30
        Lys His Lys Lys His Lys Arg Lys Arg Gly Thr Asp Gln Asp Glu Asp
                       35                  40                  45
        Gln Ser Pro Ala Ala Ser Pro Gln Ser Gly Glu Gly Ser Ser Ser
                 50                  55                  60
        Lys Pro Ala Leu Lys Leu Lys Ile Lys Ile Gly Gly Gln Thr Val Glu
         65                  70                  75                  80
        Lys Asn Val Thr Lys Leu Lys Gln Gln Arg Pro Pro Pro Asp Pro
                           85                  90                  95
        Ser Glu Ala Asp Leu Ala Glu Leu Leu Met Lys Pro Asn Ser Gly Asp
                       100                 105                 110
        Thr Ser Ala Asp Ser Asp Asp Glu Glu Glu Ala Trp Leu Glu Ala Leu
                       115                 120                 125
        Glu Ser Gly Arg Leu Glu Glu Val Asp Asp Glu Leu Arg Lys Met Lys
                       130                 135                 140
        Asp Pro Thr Leu Met Thr Ala Arg Gln Arg Ala Leu Leu Glu Ser Lys
        145                 150                 155                 160
        Ser Gln Lys Asp Glu Val Pro Ala Thr Gly Met Ala Gly Val Arg Gly
                       165                 170                 175
        Ala Arg Gln Arg Asp Val Arg Gly Asp Asp Ser Ala Ala Asp Ala Ala
                       180                 185                 190
        Gly Gln Lys Ala Glu Ala Ala Gly Arg Arg Glu Glu Arg Glu Gly Glu
                       195                 200                 205
        Glu Ala Asp Asp Arg Ala Ser Ala Gln Glu Val Arg Leu Glu Ala Glu
                       210                 215                 220
        Gly Gln Gln Glu Val Gly Gln Glu Glu Arg Tyr Ser Gln Gly Val Ala
        225                 230                 235                 240
        Gly Gln His Ala Gly Arg His Ala Ala Leu Val Ser Arg Arg Arg Cys
                       245                 250                 255
        Val Pro Ala Val Gly Ser Arg Gly Pro Gly Val Pro Arg Glu Asp Asp
                       260                 265                 270
        Val Arg His
                275

<210> SEQ ID NO 11
<211> LENGTH: 1942
<212> TYPE: DNA
<213> ORGANISM: Ixodes scapularis

<400> SEQUENCE: 11
cgatgcaggc gatgacgggc tttgcggtgc agttcaacaa aaacagtttc gggctgactc      60
cagctcagcc gctgcagttg cagattcccc tgcagcccaa cttcccagct gatgcgagct     120
tgcagctggg aaccaacggt cccgtgcaga agatggaccc cctcaccaac cttcaggtgg     180
ccatcaagaa caatgtggac gtgttctact tcagctgcct ggtgcccatg cacgtgctga     240
gcacggagga cggcctgatg gacaagcggg tgttcctggc cacctggaaa gacatccccg     300
cccaaaacga ggtccagtac accctcgaca cgtcaacctc actgcagaca caagtttccc     360
agaagctgca gaacaacaac attttcacga tagccaagag gaacgtggac ggccaggaca     420
tgctgtacca gtccctgaag ctcaccaacg gcatttgggt gttggcggag ctcaagatac     480
agcccggcaa tccaaggatc acgttgtctt tgaagacaag agcacctgaa gtggcagcag     540
```

-continued

```
gtgtacaaca aacttacgaa ctcattctac acagctgagg ctgctgtgaa tgaaactctt      600
ctcccacccc cttcttttga tggcagtcaa tgtctcgttt cattttcttg ttttcttttg      660
cggcgtgcta cggaacaagg tcctacattc ccaagttata tggtgttgtc gcgtaggggg      720
cagagtgccg ctgagcccgc gacagccttg tttctgagga gagccgaacg caccacttcg      780
aaaaagaaaa agtgaaaacg gaaaaatgaa aaattttcca gttgcttcaa attaacattc      840
ctcgtagtca gtctgtggcc gttgagtttg tgtaaagaa gaaaaggtg tctcttttag        900 tgaaaatggt tgcttttat tggtatcccc tatcacaccg agcacgaaca taagaaatcc       960
tgacaaggat tctcctttag ttgtattatg gtggctggag cacacgaggc acctgttgcc     1020
aattcgaccc agcaaatgcc caattctcaa gatttgagtt cattgaggtt gttttgctcc     1080 tccccccca cccccaact tgtcgttgg attgtctaac agtgtaaatg ggcgacgact        1140
cgttattctt ttttcttca ttctttcttt tgttgtcac gcgccccggg ggacgcgaca        1200
caacttatgt gcataattga ttttcacagg ctgcgacgca gtctgtaaaa gaaggggaag     1260
tgaaactctg ctccgccgct gctagtgtca tcacgggacg accatcgcgt tttctctgac     1320
tatttaaaca aaactgcata gcttagggggg cagtctgtgc aaagtggaac aaccaaactg    1380
agccctgccc tttcggtgtg tgtacaagca tctctgtgta acatgaacta ctttacatga    1440
actacattgc atgaacggga gaagtttagt tgtttttttg ttttttttt caggtgacta      1500 tgtcaacaga ttagaaccat ttttggaac ggctggaaag ataaccgctc attttgtttc     1560
tactaaaaga ctacgaaaag tgttgacttt ttgcatcggt ttggcaacgt ttgtttggca    1620
tgcatgtagt tgagcgtaat ggtatcaccc ctcgtaaaca ataacagtgc aatggagcag   1680
tactgtagtg tccattaaag agcgagagtt tggttaaagg ttgttaattg aggtccgtgt    1740
tatcctttga gtaggagagc ggcactttt gcaaatagcg ctgctggggg cgtcatatct    1800
gccctccaaa acatgcacat tttaagtgtg aattgttgcg gcggcttgta caagtatgtg   1860
tgttatgtgt agaaaagaa ctcttaatta aaatatttgt ggccaaaacg tcaaaaaaaa    1920
aaaaaaaaaa aaaaaaaaaa aa                                              1942
```

<210> SEQ ID NO 12
<211> LENGTH: 191
<212> TYPE: PRT
<213> ORGANISM: Ixodes scapularis

<400> SEQUENCE: 12

```
Met Gln Ala Met Thr Gly Phe Ala Val Gln Phe Asn Lys Asn Ser Phe
1               5                   10                  15

Gly Leu Thr Pro Ala Gln Pro Leu Gln Leu Gln Ile Pro Leu Gln Pro
            20                  25                  30

Asn Phe Pro Ala Asp Ala Ser Leu Gln Leu Gly Thr Asn Gly Pro Val
        35                  40                  45

Gln Lys Met Asp Pro Leu Thr Asn Leu Gln Val Ala Ile Lys Asn Asn
    50                  55                  60

Val Asp Val Phe Tyr Phe Ser Cys Leu Val Pro Met His Val Leu Ser
65                  70                  75                  80

Thr Glu Asp Gly Leu Met Asp Lys Arg Val Phe Leu Ala Thr Trp Lys
                85                  90                  95

Asp Ile Pro Ala Gln Asn Glu Val Gln Tyr Thr Leu Asp Asn Val Asn
            100                 105                 110

Leu Thr Ala Asp Gln Val Ser Gln Lys Leu Gln Asn Asn Asn Ile Phe
        115                 120                 125
```

```
Thr Ile Ala Lys Arg Asn Val Asp Gly Gln Asp Met Leu Tyr Gln Ser
    130                 135                 140

Leu Lys Leu Thr Asn Gly Ile Trp Val Leu Ala Glu Leu Lys Ile Gln
145                 150                 155                 160

Pro Gly Asn Pro Arg Ile Thr Leu Ser Leu Lys Thr Arg Ala Pro Glu
                165                 170                 175

Val Ala Ala Gly Val Gln Gln Thr Tyr Glu Leu Ile Leu His Ser
            180                 185                 190

<210> SEQ ID NO 13
<211> LENGTH: 1428
<212> TYPE: DNA
<213> ORGANISM: Ixodes scapularis
<220> FEATURE:
<221> NAME/KEY: misc_feature
<222> LOCATION: (701)..(701)
<223> OTHER INFORMATION: n is a, c, g, or t

<400> SEQUENCE: 13
cgcgccgtgc agaagctgcg tcgggaggtt gagaaggcaa agaggaccct gtccactgct      60
caccaggcca ggatcgagat tgaatcgttc ttcgagggag aggacttcag tgagaccctg     120
actcgtgcta gtttgagga gctgaacatg gaccttttcc gttccaccat gaagcctgtt     180
cagaaggtac tcgaggatgg tgacctcaag aagactgatg tggacgagat gtgcttgtc      240
ggaggttcca ccaggatccc caaggttcaa cagctggtca aggagttctt caatggcaag     300
gaacccaccc gtggcatcaa ccccgacgaa gcagtcgcct acggtgccgc cgtgcaggct     360
ggagtcctcg gcggagagga agacactggg gacctcgtgc tgttggacgt gaaccctctg     420
accctcggca tcgagacagt ggggaggcgtc atgacgaaac tgatcccccg taacacagtc     480
atccccacga agaagtctca gatcttctcc acggcctcgg acgagcagag cactgtcacc     540
atccaggtct ttgaggggga gcgtcccctg acaaaggaca accaccagct gggcaagttc     600
gacctgactg gcatcccacc tgctcctcga ggtgtgcccc aaatcgaggt gaccttcgag     660
attgacgtca acggtatcct gcgggtcagt gcagaggaca ngggtacagg caacaagcag     720
aagatcacca tcaacaatga ccagaacagg ctgacgcctg aggacatcga gaggatggta     780
aaggacgccg aaaagtttgc cgacgaggac aagaaggtca aggagaaggt ggaggcccgc     840
aacgaactgg agtcttatgc ctactccctc aagaaccaga ttggagacaa ggagaagatg     900
ggaggcaagc tctccgacga ggacaagaag actattgagc aagctgtgga cgagaaaatc     960
aaatggctgg agcagcacag tgacgctgat gcggaagaac tcaaggaaca gaagaaacag    1020
ctggctgata ctgtgcagcc gattgtagcc aagctgtacc tgcaggagg cacccccaccg    1080
ccgacggaca agatgactc tacaaaggac gagttgtaaa acaaggcca gatctcttgg      1140
gtacagcgaa aggcatgggg cagcagcatt atcacaagtc atctgttacg atcatgagct    1200
catcatttca ccacctctac agtgctgctg ctgcctgcct tttggctggt tgagtgttct    1260
tggacctatt taccatgatc attctctgta caaaaacaat tctttctgtg ttttttttt      1320
tttcgttgta gtaacttaag ttatacagat gtcttctact gggtgggctt tctccatgag    1380
tgggagggg ctgggtgtca aataaaagtg tttctattaa aaaaaaaa                   1428

<210> SEQ ID NO 14
<211> LENGTH: 372
<212> TYPE: PRT
<213> ORGANISM: Ixodes scapularis
<220> FEATURE:
```

```
<221> NAME/KEY: misc_feature
<222> LOCATION: (234)..(234)
<223> OTHER INFORMATION: Xaa can be any naturally occurring amino acid

<400> SEQUENCE: 14

Arg Ala Val Gln Lys Leu Arg Arg Glu Val Glu Lys Ala Lys Arg Thr
1               5                   10                  15

Leu Ser Thr Ala His Gln Ala Arg Ile Glu Ile Glu Ser Phe Phe Glu
            20                  25                  30

Gly Glu Asp Phe Ser Glu Thr Leu Thr Arg Ala Lys Phe Glu Glu Leu
        35                  40                  45

Asn Met Asp Leu Phe Arg Ser Thr Met Lys Pro Val Gln Lys Val Leu
    50                  55                  60

Glu Asp Gly Asp Leu Lys Lys Thr Asp Val Asp Glu Ile Val Leu Val
65                  70                  75                  80

Gly Gly Ser Thr Arg Ile Pro Lys Val Gln Gln Leu Val Lys Glu Phe
                85                  90                  95

Phe Asn Gly Lys Glu Pro Thr Arg Gly Ile Asn Pro Asp Glu Ala Val
            100                 105                 110

Ala Tyr Gly Ala Ala Val Gln Ala Gly Val Leu Gly Gly Glu Glu Asp
        115                 120                 125

Thr Gly Asp Leu Val Leu Leu Asp Val Asn Pro Leu Thr Leu Gly Ile
130                 135                 140

Glu Thr Val Gly Gly Val Met Thr Lys Leu Ile Pro Arg Asn Thr Val
145                 150                 155                 160

Ile Pro Thr Lys Lys Ser Gln Ile Phe Ser Thr Ala Ser Asp Glu Gln
                165                 170                 175

Ser Thr Val Thr Ile Gln Val Phe Glu Gly Glu Arg Pro Leu Thr Lys
            180                 185                 190

Asp Asn His Gln Leu Gly Lys Phe Asp Leu Thr Gly Ile Pro Pro Ala
        195                 200                 205

Pro Arg Gly Val Pro Gln Ile Glu Val Thr Phe Glu Ile Asp Val Asn
    210                 215                 220

Gly Ile Leu Arg Val Ser Ala Glu Asp Xaa Gly Thr Gly Asn Lys Gln
225                 230                 235                 240

Lys Ile Thr Ile Asn Asn Asp Gln Asn Arg Leu Thr Pro Glu Asp Ile
                245                 250                 255

Glu Arg Met Val Lys Asp Ala Glu Lys Phe Ala Asp Glu Asp Lys Lys
            260                 265                 270

Val Lys Glu Lys Val Glu Ala Arg Asn Glu Leu Glu Ser Tyr Ala Tyr
        275                 280                 285

Ser Leu Lys Asn Gln Ile Gly Asp Lys Glu Lys Met Gly Gly Lys Leu
    290                 295                 300

Ser Asp Glu Asp Lys Lys Thr Ile Glu Gln Ala Val Asp Glu Lys Ile
305                 310                 315                 320

Lys Trp Leu Glu Gln His Ser Asp Ala Asp Ala Glu Glu Leu Lys Glu
                325                 330                 335

Gln Lys Lys Gln Leu Ala Asp Thr Gln Pro Ile Val Ala Lys Leu
            340                 345                 350

Tyr Pro Ala Gly Gly Thr Pro Pro Thr Asp Lys Asp Asp Ser Thr
        355                 360                 365

Lys Asp Glu Leu
    370
```

<210> SEQ ID NO 15
<211> LENGTH: 1847
<212> TYPE: DNA
<213> ORGANISM: Ixodes scapularis
<220> FEATURE:
<221> NAME/KEY: misc_feature
<222> LOCATION: (1814)..(1814)
<223> OTHER INFORMATION: n is a, c, g, or t

<400> SEQUENCE: 15

| | | | | | |
|---|---|---|---|---|---|
| cgacgtgttt | gtgagtgcag | cggtgaactg | gacggtgtcg | tggccacgcg | atggcagcgg | 60 |
| cggtgatgaa | ctgcctacgg | actgcgcttt | taggcgctct | cgtcgtccaa | ctctacgcca | 120 |
| cgcagatagg | tcaccggaaa | ttcgagtaca | agtacagttt | caagggaccc | tacctggcgc | 180 |
| agaaggatgg | atcggtgcct | ttctgggagt | acggcggcaa | ttgcatcgcc | agtgaggaga | 240 |
| tggttcggat | cacgccctcc | ctgaagagca | agaaaggatc | catctggtcc | aagctgccga | 300 |
| catcgttccc | ttggtgggag | gtggagctgg | tgttccgcac | cacgggtacg | ggcaggatag | 360 |
| gagctgacgg | cctggccttc | tggtacacag | acaagaagca | ggcggagggt | cctgtctttg | 420 |
| gaagcagcga | caagtggact | ggcctggcca | tcttcttcga | ttccttcgac | aatgataaca | 480 |
| agcacaacaa | cccatacatc | atgggcatgg | tgaacgatga | aacaaaagcc | tacgatcatg | 540 |
| agagtgacgg | tgccaaccaa | cagctagcgg | gatgccagcg | ggacttccgc | aacaagcctt | 600 |
| accctgtcag | ggccaagata | gaatacttca | acaacattct | cacggtgctg | ttccacaacg | 660 |
| gcaacaccaa | caacgacggt | gactacgaga | tgtgcttccg | tgcggagaac | gtgttcctgc | 720 |
| cgaccaacgg | ccactttggg | gtgtccgccg | ccacgggggg | cctggcagac | gaccacgacg | 780 |
| ccctcaagtt | cctgacgacg | agcctgcatg | cggagggcac | gcagccggcc | ctggcccagg | 840 |
| gtatggccga | ctcagagaag | gagaagttct | ccaaggagta | tgaagtatac | aaggacaagc | 900 |
| tggaaaagca | gaaggaggag | taccggaaga | cgcacccgga | ggaggccgct | aagcaggcca | 960 |
| tggagcacgc | ccccgagcag | gcctacgaca | cgcagcagca | gcgcgagctg | cgccagatct | 1020 |
| tcgagggcca | gagccacaaa | ttgtttgagg | ggctcaaggc | actgcaccgc | aagctggacg | 1080 |
| aggtgctcgg | gcgccaggag | cgcacccctgt | cgctggtgtc | ggctggcggc | gccggcgtgg | 1140 |
| ccgtgggcgg | tgttccgcca | ccgcagatgg | gtggagtgcc | gtcgctgcag | aggcacgaag | 1200 |
| cagagtccct | gctgagcagc | cagcgggagc | tgctgcagac | ggtggctcag | gtcaagagct | 1260 |
| tgtggccga | ggtgcatcaa | cgcacggcca | ccctgcaaca | ccaggggggcg | ggaggcaccc | 1320 |
| agggcctcac | ggccgagcag | ctgcaagtgc | tccaccaggt | gcgggacagc | gtggccagca | 1380 |
| tgcaccggga | cgtctccaac | aaccagccgc | agaggactgg | ctgcgcgaca | tcctgtctca | 1440 |
| gcactaccca | cttcttgctg | tttgcaacgt | tgcagttggc | tgtcacgctg | ggctacttgg | 1500 |
| tgtacaggag | cagcaaagag | gcggcggcca | agaagttcta | ctgagtgcag | atctcgagcc | 1560 |
| ttgccttgcc | ctcccctccc | atggagtgga | ccttaacccc | acagactgcc | agaaaccagt | 1620 |
| gttgccagag | gagcccccct | cccttcttat | tgggtggggt | gccacagcca | tcacccattc | 1680 |
| ttcgagacaa | ggccactgtt | tggggggagg | ggcaagagat | tcatccgggg | tgcgcaacaa | 1740 |
| aacatggccg | tacagaggga | ggggtgctcc | agaactgggt | cccagccaca | tcgttgcgtg | 1800 |
| ggagcgcctt | tctncctcac | tctaaaaaaa | aaaaaaaaa | aaaaaaa | | 1847 |

<210> SEQ ID NO 16
<211> LENGTH: 497
<212> TYPE: PRT
<213> ORGANISM: Ixodes scapularis

<400> SEQUENCE: 16

```
Met Ala Ala Ala Val Met Asn Cys Leu Arg Thr Ala Leu Leu Gly Ala
1               5                   10                  15

Leu Val Val Gln Leu Tyr Ala Thr Gln Ile Gly His Arg Lys Phe Glu
            20                  25                  30

Tyr Lys Tyr Ser Phe Lys Gly Pro Tyr Leu Ala Gln Lys Asp Gly Ser
            35                  40                  45

Val Pro Phe Trp Glu Tyr Gly Asn Cys Ile Ala Ser Glu Glu Met
    50                  55                  60

Val Arg Ile Thr Pro Ser Leu Lys Ser Lys Gly Ser Ile Trp Ser
65                  70                  75                  80

Lys Leu Pro Thr Ser Phe Pro Trp Trp Glu Val Glu Leu Val Phe Arg
                85                  90                  95

Thr Thr Gly Thr Gly Arg Ile Gly Ala Asp Gly Leu Ala Phe Trp Tyr
            100                 105                 110

Thr Asp Lys Lys Gln Ala Glu Gly Pro Val Phe Gly Ser Ser Asp Lys
            115                 120                 125

Trp Thr Gly Leu Ala Ile Phe Phe Asp Ser Phe Asp Asn Asp Asn Lys
            130                 135                 140

His Asn Asn Pro Tyr Ile Met Gly Met Val Asn Asp Gly Thr Lys Ala
145                 150                 155                 160

Tyr Asp His Glu Ser Asp Gly Ala Asn Gln Gln Leu Ala Gly Cys Gln
                165                 170                 175

Arg Asp Phe Arg Asn Lys Pro Tyr Pro Val Arg Ala Lys Ile Glu Tyr
            180                 185                 190

Phe Asn Asn Ile Leu Thr Val Leu Phe His Asn Gly Asn Thr Asn Asn
            195                 200                 205

Asp Gly Asp Tyr Glu Met Cys Phe Arg Ala Glu Asn Val Phe Leu Pro
210                 215                 220

Thr Asn Gly His Phe Gly Val Ser Ala Ala Thr Gly Gly Leu Ala Asp
225                 230                 235                 240

Asp His Asp Ala Leu Lys Phe Leu Thr Thr Ser Leu His Ala Glu Gly
                245                 250                 255

Thr Gln Pro Ala Leu Ala Gln Gly Met Ala Asp Ser Glu Lys Glu Lys
            260                 265                 270

Phe Ser Lys Glu Tyr Glu Val Tyr Lys Asp Lys Leu Glu Lys Gln Lys
            275                 280                 285

Glu Glu Tyr Arg Lys Thr His Pro Glu Glu Ala Ala Lys Gln Ala Met
290                 295                 300

Glu His Gly Pro Glu Gln Ala Tyr Asp Thr Gln Gln Arg Glu Leu
305                 310                 315                 320

Arg Gln Ile Phe Glu Gly Gln Ser His Lys Leu Phe Glu Gly Leu Lys
            325                 330                 335

Ala Leu His Arg Lys Leu Asp Glu Val Leu Gly Arg Gln Glu Arg Thr
            340                 345                 350

Leu Ser Leu Val Ser Ala Gly Gly Ala Gly Val Ala Val Gly Gly Val
            355                 360                 365

Pro Pro Pro Gln Met Gly Gly Val Pro Ser Leu Gln Arg His Glu Ala
370                 375                 380

Glu Ser Leu Leu Ser Ser Gln Arg Glu Leu Leu Gln Thr Val Ala Gln
385                 390                 395                 400

Val Lys Ser Phe Val Ala Glu Val His Gln Arg Thr Ala Thr Leu Gln
                405                 410                 415
```

```
His Gln Gly Ala Gly Gly Thr Gln Gly Leu Thr Ala Glu Gln Leu Gln
            420                 425                 430

Val Leu His Gln Val Arg Asp Ser Val Ala Ser Met His Arg Asp Val
        435                 440                 445

Ser Asn Asn Gln Pro Gln Arg Thr Gly Cys Ala Thr Ser Cys Leu Ser
    450                 455                 460

Thr Thr His Phe Leu Leu Phe Ala Thr Leu Gln Leu Ala Val Thr Leu
465                 470                 475                 480

Gly Tyr Leu Val Tyr Arg Ser Ser Lys Glu Ala Ala Lys Lys Phe
                485                 490                 495

Tyr

<210> SEQ ID NO 17
<211> LENGTH: 2475
<212> TYPE: DNA
<213> ORGANISM: Ixodes scapularis
<220> FEATURE:
<221> NAME/KEY: misc_feature
<222> LOCATION: (1342)..(1342)
<223> OTHER INFORMATION: n is a, c, g, or t
<220> FEATURE:
<221> NAME/KEY: misc_feature
<222> LOCATION: (1388)..(1388)
<223> OTHER INFORMATION: n is a, c, g, or t

<400> SEQUENCE: 17
catcactagt agcgagacac gtgcgtaaaa atggggccca aaacgctgtc taagcagccc      60
gctaaagctt cttcatccac ttccaagcgc accgccggcc ccacaataag caagcagacg     120
gaggacagcg atgacgaagg gtcaagcagc gcctactccg acttggagga ctccgaagga     180
gccgacagca gcgactcgaa cgatttgtcg gacacggagg cgtcggagga tgactacgat     240
gactcccaag acgaagaaaa cacgaagatt actttgactg gggtggaggg gaaggacctt     300
gagttgaggg ggaaggacca ggaggcaccg gtggagtctg gcaaaaggtc ggcatggcac     360
cggcagcaag aggacgccaa ggaggacaga cgaacgcaag tggtggaaga tgaatatgcc     420
tttgactctt ccgacgaaga ggacgttcgc aacacggttg gcaacattcc tctggagtgg     480
tacgagcact atccgcacat cggttatgat ctggaaggca agccaatcct gaagccgcct     540
cgggttagtg acctggacga cttcctgagg aaaatggatg accccaacta ttggaggacg     600
gtgaaggaca agagcacggg acaggacgtt gtcctgaccg acgaagatgt ggacctgatt     660
cagaggctgc agaaaggaca gttccccagc tcgacgactg accttacga gccatttgag     720 gacatctttt cgcacgagac catgatccac ccggtgacca ggcaccctcc ccagaaacgc     780
agcttcgtgc cttcaaggat agaaaaagca atggtgtcaa agatggtgca cgcaatcaag     840
atgggctgga tcaagccccg agtaaagaag catgacccag aaagattcag cctcctgtgg     900
gacaaggatg actcgacagc gggcagcaat gagcgaatgc agcgccacat cccggcaccc     960
aagatgaagc tgccgggtca tgaggagtct acaacccgc cggccgaata cctcttcacc    1020
gaggaagagg aggccaagtg gagagagcag gagcccgaag aacggcgcat aaacttcctg    1080
cccgccaagt acccatgtct gcgcgcagtc ccagcctacg aacgcttcat tgaggagagg    1140
tttgagcgct gtctggatct ctacttgtgc ccgaggcagc ggaagatgag ggtgaatgtg    1200
gatgcagagg acctgattcc tcagctgccc aaacccaagg acctgcagcc tttcccaagc    1260
attcagtcta ttgtctatga gggtcatacg gactgtgtcc tctgcctgtc tttggagcct    1320
gcgggacagt tctttgcatc anggtccgag gacggcaccg ttcgcatttg ggagctcttg    1380
```

-continued

```
acgggcangt gcctcaagaa gttccagttc gaggcgcccg tgaagagcgt ggcctggtgt    1440
ccagttgtcg ttcccatgaa actctgcgtg acaagactg tttccatgct ggatgccgga    1500
gttacggaca aactgctgcc gttcaccacg ggacaccgag ttgtctgccc tccccgaaga    1560
gtcctcgggc caggcggcgg tagtggagtg ggagcagacg tcggcctcct ctccagagtt    1620
cctctcccgg ggggagcgtc tgcgggtcgt tcaccgccac ggtgtggtgc aggtgacgtg    1680
gcactcgagg ggagactact ttgccactgt cacggacgag ggacaggcca ccgtgcttgt    1740
ccatcagttg tccacgcggc ggttcgcagg ctccccttca gcaaggcgaa gggcggggtg    1800
tcccgggtgc tgttccaccc gctgcgcccc ttcctgctgg tggcgtgcca gcgcacagtg    1860
cgggtctacc acctgctcaa gcaggagctg gccaagaggc tcacatccaa ttgcaagtgg    1920
atctcgtgca tgggccgtcc accccaggt gacaatctgc tgatcggcac gtacgagaag    1980
cggctgatgt ggttcgatct ggacctctcg accaaaccgt accagcagct gcgcatacac    2040
aatgccgcca tccgcagtgt ggcgttccat ccgcgctatc cactgtttgc gtccgccggc    2100
gacgatcgca gcgtgatcgt ttcgcacggt atggtgtaca atgatttact gcaaaaccca    2160
ctgatcgtgc cactgagacg gctgaagaac catgccatca gcaagggtat gggtgtgttg    2220
gactgcgcct tccatcccca ccagccgtgg atagtcacgg ccggagcaga cagcacgctg    2280
cggctcttca cctaagccgg gacgtcgtct ggtgtacata gtgaatcgtc aagaccgtgc    2340
caataaaagg actccacacc taaaaaaaaa aaaaaaaaaa aaaaaaaaaa aaaaaaaaa    2400 aaaaaaaaaa aaaaaaaaaa aaaaaaaaaa aaaaaaaaaa aaaaaaaaaa aaaaaaaaaa    2460
aaaaaaaaaa aaaaa                                                    2475
```

<210> SEQ ID NO 18
<211> LENGTH: 754
<212> TYPE: PRT
<213> ORGANISM: Ixodes scapularis
<220> FEATURE:
<221> NAME/KEY: misc_feature
<222> LOCATION: (438)..(438)
<223> OTHER INFORMATION: Xaa can be any naturally occurring amino acid
<220> FEATURE:
<221> NAME/KEY: misc_feature
<222> LOCATION: (453)..(453)
<223> OTHER INFORMATION: Xaa can be any naturally occurring amino acid

<400> SEQUENCE: 18

```
Met Gly Pro Lys Thr Leu Ser Lys Gln Pro Ala Lys Ala Ser Ser Ser
1               5                   10                  15

Thr Ser Lys Arg Thr Ala Gly Pro Thr Ile Ser Lys Gln Thr Glu Asp
            20                  25                  30

Ser Asp Asp Glu Gly Ser Ser Ala Tyr Ser Asp Leu Glu Asp Ser
        35                  40                  45

Glu Gly Ala Asp Ser Ser Asp Ser Asn Asp Leu Ser Asp Thr Glu Ala
    50                  55                  60

Ser Glu Asp Asp Tyr Asp Asp Ser Gln Asp Glu Glu Asn Thr Lys Ile
65                  70                  75                  80

Thr Leu Thr Gly Val Glu Gly Lys Asp Leu Glu Leu Arg Gly Lys Asp
                85                  90                  95

Gln Glu Ala Pro Val Glu Ser Gly Lys Arg Ser Ala Trp His Arg Gln
            100                 105                 110

Gln Glu Asp Ala Lys Glu Asp Arg Arg Thr Gln Val Val Glu Asp Glu
        115                 120                 125
```

-continued

```
Tyr Ala Phe Asp Ser Ser Asp Glu Glu Asp Val Arg Asn Thr Val Gly
    130                 135                 140
Asn Ile Pro Leu Glu Trp Tyr Glu His Tyr Pro His Ile Gly Tyr Asp
145                 150                 155                 160
Leu Glu Gly Lys Pro Ile Leu Lys Pro Arg Val Ser Asp Leu Asp
            165                 170                 175
Asp Phe Leu Arg Lys Met Asp Asp Pro Asn Tyr Trp Arg Thr Val Lys
                180                 185                 190
Asp Lys Ser Thr Gly Gln Asp Val Leu Thr Asp Glu Asp Val Asp
        195                 200                 205
Leu Ile Gln Arg Leu Gln Lys Gly Gln Phe Pro Ser Ser Thr Thr Asp
    210                 215                 220
Pro Tyr Glu Pro Phe Glu Asp Ile Phe Ser His Glu Thr Met Ile His
225                 230                 235                 240
Pro Val Thr Arg His Pro Pro Gln Lys Arg Ser Phe Val Pro Ser Arg
                245                 250                 255
Ile Glu Lys Ala Met Val Ser Lys Met Val His Ala Ile Lys Met Gly
            260                 265                 270
Trp Ile Lys Pro Arg Val Lys Lys His Asp Pro Glu Arg Phe Ser Leu
    275                 280                 285
Leu Trp Asp Lys Asp Asp Ser Thr Ala Gly Ser Asn Glu Arg Met Gln
290                 295                 300
Arg His Ile Pro Ala Pro Lys Met Lys Leu Pro Gly His Glu Glu Ser
305                 310                 315                 320
Tyr Asn Pro Pro Ala Glu Tyr Leu Phe Thr Glu Glu Glu Ala Lys
            325                 330                 335
Trp Arg Glu Gln Glu Pro Glu Glu Arg Arg Ile Asn Phe Leu Pro Ala
                340                 345                 350
Lys Tyr Pro Cys Leu Arg Ala Val Pro Ala Tyr Glu Arg Phe Ile Glu
        355                 360                 365
Glu Arg Phe Glu Arg Cys Leu Asp Leu Tyr Leu Cys Pro Arg Gln Arg
    370                 375                 380
Lys Met Arg Val Asn Val Asp Ala Glu Asp Leu Ile Pro Gln Leu Pro
385                 390                 395                 400
Lys Pro Lys Asp Leu Gln Pro Phe Pro Ser Ile Gln Ser Ile Val Tyr
                405                 410                 415
Glu Gly His Thr Asp Cys Val Leu Cys Leu Ser Leu Glu Pro Ala Gly
            420                 425                 430
Gln Phe Phe Ala Ser Xaa Ser Glu Asp Gly Thr Val Arg Ile Trp Glu
        435                 440                 445
Leu Leu Thr Gly Xaa Cys Leu Lys Lys Phe Gln Phe Glu Ala Pro Val
    450                 455                 460
Lys Ser Val Ala Trp Cys Pro Val Val Pro Met Lys Leu Cys Val
465                 470                 475                 480
Asp Lys Thr Val Ser Met Leu Asp Ala Gly Val Thr Asp Lys Leu Leu
                485                 490                 495
Pro Phe Thr Thr Gly His Arg Val Val Cys Pro Arg Arg Val Leu
            500                 505                 510
Gly Pro Gly Gly Gly Ser Gly Val Gly Ala Asp Val Gly Leu Leu Ser
        515                 520                 525
Arg Val Pro Leu Pro Gly Gly Ala Ser Ala Gly Arg Ser Pro Pro Arg
    530                 535                 540
Cys Gly Ala Gly Asp Val Ala Leu Glu Gly Arg Leu Leu Cys His Cys
```

```
                    545                 550                 555                 560
His Gly Arg Gly Thr Gly His Arg Ala Cys Pro Ser Val Val His Ala
                565                 570                 575

Ala Val Arg Arg Leu Pro Phe Ser Lys Ala Lys Gly Gly Val Ser Arg
                580                 585                 590

Val Leu Phe His Pro Leu Arg Pro Phe Leu Leu Val Ala Cys Gln Arg
                595                 600                 605

Thr Val Arg Val Tyr His Leu Leu Lys Gln Glu Leu Ala Lys Arg Leu
                610                 615                 620

Thr Ser Asn Cys Lys Trp Ile Ser Cys Met Gly Arg Pro Pro Gly
625                 630                 635                 640

Asp Asn Leu Leu Ile Gly Thr Tyr Glu Lys Arg Leu Met Trp Phe Asp
                645                 650                 655

Leu Asp Leu Ser Thr Lys Pro Tyr Gln Gln Leu Arg Ile His Asn Ala
                660                 665                 670

Ala Ile Arg Ser Val Ala Phe His Pro Arg Tyr Pro Leu Phe Ala Ser
                675                 680                 685

Ala Gly Asp Asp Arg Ser Val Ile Val Ser His Gly Met Val Tyr Asn
                690                 695                 700

Asp Leu Leu Gln Asn Pro Leu Ile Val Pro Leu Arg Arg Leu Lys Asn
705                 710                 715                 720

His Ala Ile Ser Lys Gly Met Gly Val Leu Asp Cys Ala Phe His Pro
                725                 730                 735

His Gln Pro Trp Ile Val Thr Ala Gly Ala Asp Ser Thr Leu Arg Leu
                740                 745                 750

Phe Thr

<210> SEQ ID NO 19
<211> LENGTH: 447
<212> TYPE: DNA
<213> ORGANISM: Ixodes scapularis

<400> SEQUENCE: 19
caaagatgct gctgttctgc ccgacgtgcg ccaacatcct cattgtggaa caaggcttgg      60
agtgcttccg tttcgcctgc aacacatgcc cctacgtgca caacatcaag gcgaagatgt     120
cgaatcggaa gtacccgcgg ctcaaggacg tggacgacgt gctcggcggt gcagccgcct     180
gggagaatgt tgactcgacc gaagagaagt gccccaagtg tggccatgag cgggcctatt     240
ttatgcagat ccagactagg tcggccgacg agcccatgac caccttctac aagtgctgca     300
accagctctg tggccaccag tggagggact gacagatggc ggctttgacg aactcatgcc     360
cgtgcaaaat gcgtcggggg gagagagttt tggaataaaa catgcgcctt actttcataa     420
aaaaaaaaaa aaaaaaaaa aaaaaaa                                          447

<210> SEQ ID NO 20
<211> LENGTH: 108
<212> TYPE: PRT
<213> ORGANISM: Ixodes scapularis

<400> SEQUENCE: 20

Met Leu Leu Phe Cys Pro Thr Cys Ala Asn Ile Leu Ile Val Glu Gln
1               5                   10                  15

Gly Leu Glu Cys Phe Arg Phe Ala Cys Asn Thr Cys Pro Tyr Val His
                20                  25                  30

Asn Ile Lys Ala Lys Met Ser Asn Arg Lys Tyr Pro Arg Leu Lys Asp
```

```
                35                  40                  45
Val Asp Asp Val Leu Gly Gly Ala Ala Ala Trp Glu Asn Val Asp Ser
 50                  55                  60

Thr Glu Glu Lys Cys Pro Lys Cys Gly His Glu Arg Ala Tyr Phe Met
 65                  70                  75                  80

Gln Ile Gln Thr Arg Ser Ala Asp Glu Pro Met Thr Thr Phe Tyr Lys
                 85                  90                  95

Cys Cys Asn Gln Leu Cys Gly His Gln Trp Arg Asp
            100                 105

<210> SEQ ID NO 21
<211> LENGTH: 1567
<212> TYPE: DNA
<213> ORGANISM: Ixodes scapularis
<220> FEATURE:
<221> NAME/KEY: misc_feature
<222> LOCATION: (785)..(785)
<223> OTHER INFORMATION: n is a, c, g, or t

<400> SEQUENCE: 21 cccccaggc gcagggcttc gttcaggtcg accaggggc cctccccgca gccccgagg      60
agcgccacct ggcaagcatg caggtcaatg gatatgagaa ccccacctac aagtacttcg    120
aggccaacac caactgagcg gccacgcccc caggggaggg ggaaaagggg gcggacggac    180
gtattgtgcc tgctgcgggc tgcgggatta gctcgtcccg cgttgttccg ggagccagtt    240
ggtttgcctc gcgtcttagg agtaggcacg gcctcccttc tgcacccggt caaggaccat    300
ggttgttggg gacacgagcg gcgtggggcg cagccagcct gagctttggg tcccggtacc    360
acggcaaacc gtttgttccc acccgcggaa tgaaaatttt gtttgcctca gtttctttcg    420
aatcgagcgt cggcgccgcc tccgacagcc ccgagtgcac tctgtctgtt gcgaaagacc    480
aatggagtag ttgacactcg ggtcgcagct cgaacaagct cccgtaaaac gctacttaac    540
cggggccggc gaccgagcgt agagcttgct gtgcgtagtt gtggataaaa cttttttttt    600
ttgtgtgtgt gcttggtcac agacaatggg cagcttccga cgttagccac gcgccacacg    660
ctcgcctttg ttttcttctt ctcgcggttg tcatacttag tttccattgg cgggttaaca    720
ttccagtccg ggcgggcgcc cccgttcagg cgcgtcctga tcaaaattga gcatttggtt    780
gtgcngtgca tttattggcc gcagcagggg gttcccgggt gcacctggtg tcgtgacacg    840
catgtcgtga cttccccctc agacggttgt ccttgctcat ggctcgttca cacctctagt    900
gctggtagtc tctgttgctt aggtttgtag gagcacacta cagcagaggg tgtcacaaag    960
ttttctaagc tgtatataca tgaggaaaac attgcgttgc acacacgcga gtttcggcct   1020
gttttagtt gggacagtga acgttttttg tacaggttat tatgtagtgc ctacatttgt   1080
atgtgccagc tgcatgtgtt ttcctgcatg tggggaagcc tccgtgctgc cccgagctgt   1140
gtgcggcccc tcctgagttt ccatgtgcca tgtgcccagc ctagggtgaa ctgggggtgc   1200
agatgccctt gcgcacggtg tgccccggcg agcattgtgt gtccgtaggc catcgacgct   1260
attcatgcga aattaatgtg gtcacagctg tcattgtctc agtgaacata tcatatgtcc   1320
aaatttgtct cccctgtcag tgtgtgcttc tcttggttct acacttgcct gcattttgt    1380
tagtttgccg gactgtcctt ttcggtccca ggtcgacagc aggctataac aacaattccg   1440
gtattttcca gtatcgggtc acaccaggtg taacctattg tgcatgtagt gtaacttgag   1500
tggaaaagct aaaataaaaa tttgcaagag tctcactaaa aaaaaaaaaa aaaaaaaaa   1560
aaaaaaa                                                            1567
```

-continued

<210> SEQ ID NO 22
<211> LENGTH: 44
<212> TYPE: PRT
<213> ORGANISM: Ixodes scapularis

<400> SEQUENCE: 22

Pro Gln Ala Gln Gly Phe Val Gln Val Asp Gln Gly Ala Leu Pro Ala
1               5                   10                  15

Ser Pro Glu Glu Arg His Leu Ala Ser Met Gln Val Asn Gly Tyr Glu
            20                  25                  30

Asn Pro Thr Tyr Lys Tyr Phe Glu Ala Asn Thr Asn
        35                  40

<210> SEQ ID NO 23
<211> LENGTH: 704
<212> TYPE: DNA
<213> ORGANISM: Ixodes scapularis
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t

<400> SEQUENCE: 23
tgagaagaca ctagaggaca agttcttcga gcatgaggtg atgctgaatg tgaatgcgtt      60
catgcagcag ttccattccg gcgtttttta tgcctacgtg aagctgaagg aacaagagtg     120
ccgcaacatt gtctggattg ccgaatgcgt tgctcagcgt catcggtcca agatcgataa     180
ctacattcca atcttctagt cgctcgagga aaagaaatgg gccaattcgg tagtttgtcg     240
gtgtaatata tatatatata tatatctact tcgcaaaatt cttcagctag agtgtctatg     300
tctggttagc tgcgattgtg cgagagggga aaaaaatgta gtcagtggca tgatcaagga     360
aggaaaaaaa ttggccaata acttttacct tttgaagtta aagcaagggt taaaataatg     420
tctattttta cttcgcttta ccgtgtgctg gctattgctt tgcaaacgtt ttttaaaatt     480
tttgcagttc gtctttcttc ttttgagcac atatttattc cagagttcca atanccttt      540 atgtgtgaat gaatgactaa tccatgttgg ggttggttaa tggtgcattg ttgaaaanat     600 aaacccccaac tccagctggc ctttggaaaa aaaaaaaaaa aaaaaaaaaa aaaaaaaaa     660 aaaaaaaaaa aaaaaaaaaa aaaaaaaaaa aaaaaaaaaa aaaa                     704

<210> SEQ ID NO 24
<211> LENGTH: 681
<212> TYPE: DNA
<213> ORGANISM: Ixodes scapularis
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (467)..(467)
<223> OTHER INFORMATION: n is a, c, g, or t
<220> FEATURE:
<221> NAME/KEY: misc_feature
<222> LOCATION: (472)..(472)
<223> OTHER INFORMATION: n is a, c, g, or t
<220> FEATURE:
<221> NAME/KEY: misc_feature
<222> LOCATION: (481)..(481)
<223> OTHER INFORMATION: n is a, c, g, or t

```
<220> FEATURE:
<221> NAME/KEY: misc_feature
<222> LOCATION: (493)..(493)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (499)..(499)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (515)..(515)
<223> OTHER INFORMATION: n is a, c, g, or t
<220> FEATURE:
<221> NAME/KEY: misc_feature
<222> LOCATION: (518)..(518)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (533)..(533)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (565)..(565)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (571)..(571)
<223> OTHER INFORMATION: n is a, c, g, or t
<220> FEATURE:
<221> NAME/KEY: misc_feature
<222> LOCATION: (586)..(586)
<223> OTHER INFORMATION: n is a, c, g, or t
<220> FEATURE:
<221> NAME/KEY: misc_feature
<222> LOCATION: (593)..(593)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (611)..(611)
```

<223> OTHER INFORMATION: n is a, c, g, or t
<220> FEATURE:
<221> NAME/KEY: misc_feature
<222> LOCATION: (619)..(619)
<223> OTHER INFORMATION: n is a, c, g, or t
<220> FEATURE:
<221> NAME/KEY: misc_feature
<222> LOCATION: (623)..(623)
<223> OTHER INFORMATION: n is a, c, g, or t
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (658)..(658)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (673)..(674)
<223> OTHER INFORMATION: n is a, c, g, or t

<400> SEQUENCE: 24

```
gtcacgggat tgggaagct gtcgtctgtc gtcctgcagt ttcaaacggt ttcaccaaaa      60
acctttccgt ctcgctgtca gacgccttga accatgactg agttctggct catctcggct   120
ccgggcgaga aaacctgcca acagacttat gacaagctgc tcagcgtcac aagcaacaag   180
cagaacaacc tctcgacctg ctacaagttc caccttccgg acttgaaggt gggtacgctg   240
gatcagttgg ttggcctctc ggatgacttg ggaaagctcg acacctatgt cgaaagcatc   300
actcgaaaag tggccagcta tctgggggac gtgcttgacg accagaggga caaactagcc   360
gacaaccttc cttgccaatg gcttggggct ggaggcctac ctgaccccgg ttttcagtgg   420
gacatggcca ataccccat caagcagttc gcctcaagag catcacntga antcatcagc    480
nagcaagtgt ctnanattng accggtngaa cctcnagnag caagttanct tgnttacaac   540
aaccttnaan aacttaagnt tcaantncat ncgaaccccca aatccnccgg ggnaggccng  600
gcnttnttcc ngttagccnt ggncntnacc ttattgcgcc aagggagcca ntttgtcntt   660
gggggntcgg ganntacctt a                                             681
```

<210> SEQ ID NO 25
<211> LENGTH: 720
<212> TYPE: DNA
<213> ORGANISM: Ixodes scapularis
<220> FEATURE:
<221> NAME/KEY: misc_feature
<222> LOCATION: (488)..(488)
<223> OTHER INFORMATION: n is a, c, g, or t
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature

```
<222> LOCATION: (631)..(631)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (680)..(680)
<223> OTHER INFORMATION: n is a, c, g, or t
<220> FEATURE:
<221> NAME/KEY: misc_feature
<222> LOCATION: (692)..(692)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t
<220> FEATURE:
<221> NAME/KEY: misc_feature
<222> LOCATION: (719)..(719)
<223> OTHER INFORMATION: n is a, c, g, or t

<400> SEQUENCE: 25
ctctcagcga ctccgacgtc caaaagcaga tcaagcacat gatggctttc atcgaccagg      60
aagccaacga aaaggcagaa gaagtagacg ccaaggcagg aagaagagtt caacatcgag     120
aagggccgcc tggtcacgga gcaaaggctc aagatcatcg actactacac ccgtcgagag     180
aagcaagttg aactgcagcg caagatccaa agctccaaca tgctgaacca ggcccggctg     240
aaggtgctga aggcgggcga ggaccacatt gcgacggtgc tggaggaggc caagcgccgc     300
ctgggggaca tcaccaggga ccaggctcgc taccaagccc tcctgcagag catggttctg     360
caggcactgc ttcagctcct cgagcaggag gtggtcgtcc actgccgacc gcaagacgcc     420
gggctgctga acttggacac gctgagtgcc aagttcaagg aggccactgg ccgagaggtc     480
aagctcantg tggagcccag cctggcttcg agcagctgcg gcggagtcga gatgctctcc     540
aggcggggca agattcgcgt ctgcaacacg ctcgagtcgc ggctggacat gattgccctt     600
cagctttctg ccgcagatca agacngncct nttcggcagg naccccccaac cgcaagttca     660 tggactaggc gggctattgn ccccgccatt cnggccagtn agcttggacc gtgtttacng     720
```

PROTECTIVE ANTIGENS FOR THE CONTROL OF *IXODES* SPECIES INFESTATIONS

CROSS REFERENCE TO RELATED APPLICATION

This application claims the benefit of copending U.S. Provisional Patent Application Ser. No. 60/376,251 filed Apr. 29, 2002.

BACKGROUND OF THE INVENTION

1. Technical Field

The present invention relates to the identification of protective antigens against infestations with *Ixodes* spp. ticks, gene sequences and encoded proteins for such antigens, related vaccines and methods useful to induce an immune response, which are protective to interfere with infestations by *Ixodes* spp. ticks.

2. Background

Ticks parasitize wild, domesticated animals and humans and transmit pathogens including fungi, bacteria, viruses and protozoon. Currently, ticks are considered to be second in the world to mosquitoes as vectors of human diseases, but they are considered to be the most important vector of pathogens in North America (Parola and Raoult, 2001). *Ixodes* spp. are distributed worldwide and act as vectors of human diseases caused by *Borrelia burgdorferi* (Lyme disease), *Anaplasma phagocytophila* (human granulocytic ehrlichiosis), *Coxiella burnetti* (Q fever), *Francisella tularensis* (tularemia), *B. afzelii*, *B. lusitaniae*, *B. valaisiana* and *B. garinii*, *Rickettsia helvetica*, *R. japonica* and *R. australis*, *Babesia divergens* and tick-borne encephalitis (TBE) and Omsk Hemorrhagic fever viruses (Estrada-Peña and Jongejan, 1999; Parola and Raoult, 2001). Throughout eastern and southeastern United States and Canada, *I. scapularis* (the black legged tick) is the main vector of *B. burgdorferi* sensu stricto and *A. phagocytophila* (Estrada-Peña and Jongejan, 1999; Parola and Raoult, 2001).

Control of tick infestations is difficult and often impractical for multi-host ticks such as *Ixodes* spp. Presently, tick control is effected by integrated pest management in which different control methods are adapted to one area or against one tick species with due consideration to their environmental effects. Recently, development of vaccines against one-host *Boophilus* spp. has provided new possibilities for the identification of protective antigens for immunization against tick infestations (Willadsen, 1997; Willadsen and Jongejan, 1999; de la Fuente et al., 1999; 2000; de Vos et al., 2001). The recombinant *B. microplus* BM86 gut antigen included in commercial vaccine formulations TickGARD (Hoechst Animal Health, Australia) and Gavac (Heber Biotec S. A., Havana, Cuba) also confers partial protection against phylogenetically related *Hyalomma* and *Rhipicephalus* tick genera (de la Fuente et al., 2000; de Vos et al., 2001). However, immunization with BM86 failed to protect against the more phylogenetically distant *Amblyomma* spp. (de Vos et al., 2001). These results suggest that using Bm86 or a closely related gene for the production of vaccines against *Ixodes* spp. or other tick genera phylogenetically distant from *Boophilus* spp. (Black and Piesman, 1994) could be impractical. Therefore, the screening for novel protective antigens is necessary to identify vaccine candidates against infestations with these tick species of medical and veterinary importance. Control of ticks by vaccination would avoid environmental contamination and selection of drug resistant ticks that result from repeated acaricide application (de la Fuente et al., 1998; Garcia-Garcia et al., 1999). Anti-tick vaccines also allow for inclusion of multiple antigens in order to target a broad range of tick species and for incorporation of pathogen-blocking antigens.

Vaccination with DNA and cDNA molecules has been used to induce a protective immune response against *B. microplus* and several pathogens in laboratory animals and livestock (De Rose et al., 1999; Drew et al., 1999; van Drunen Littel-van den Hurk et al., 2001; Kofta and Wedrychowicz, 2001). A new technique, expression library immunization (ELI) in combination with sequence analysis provides an alternative approach for identification of potential vaccine antigens based on rapid screening of the expressed genes without prior knowledge of the antigens encoded by cDNA clones. ELI was first reported for *Mycoplasma pulmonis* (Barry et al., 1995) and since then has been used for unicellular and multicellular pathogens and viruses (Manoutcharian et al., 1998; Alberti et al., 1998; Brayton et al., 1998; Melby et al., 2000; Smooker et al., 2000; Moore et al., 2002; Singh et al., 2002). However, the identification of individual protective clones has not been reported and it is predicted that identification of protective antigens will be more difficult as the complexity of the genome increases.

Although several reports in the literature have demonstrated by ELI that libraries can offer a degree of protection (Barry et al., 1995; Manoutcharian et al., 1998; Alberti et al., 1998; Brayton et al., 1998; Melby et al., 2000; Smooker et al., 2000; Moore et al., 2002; Singh et al., 2002), none have applied ELI to arthropods and particularly to ticks. Several vaccines have been developed to protect humans against *Ixodes*-transmitted pathogens including TBE virus and *B. burgdorferi*. However, it is not clear whether these vaccines will protect against all pathogen strains and genotypes. The inclusion of tick immunogens in pathogen-specific vaccines could enhance their protective effect and increase efficacy (Nuttall, 1999). This transmission-blocking approach is supported by evidence that host resistance to ticks provides some protection against tick-borne transmission of viruses and *B. burgdorferi* (Wikel et al., 1997). Furthermore, vaccination against *B. microplus* has been demonstrated to contribute to the control of tick-borne diseases (de la Fuente et al., 1998; 1999).

SUMMARY OF THE INVENTION

The present invention is based upon our identification by ELI and sequence analysis of protective cDNA clones against experimental infestations with *I. scapularis*. This is the first example of the application of ELI to arthropods and particularly to ticks. The protective antigens are homologous to endopeptidases, nucleotidases, chorion proteins, vitellogenin receptors, peptidoglycan recognition proteins, glutamine-alanine rich proteins, ribosomal proteins, β-adaptin, Beta-amyloid precursor protein, Block of proliferation (Bop1), lectins, chloride channels, RNA polymerases, ATPases and heat-shock proteins. These antigens induce an immune response in vaccinated hosts that either interferes with tick development or results in a pro-feeding activity, which could be due to the expression of cDNAs encoding for tick immunosuppressants, anticoagulants and other proteins with low antigenicity and a pro-feeding activity or they could encode for proteins homologous to host proteins with anti-tick activity, which neutralization results in a tick pro-feeding activity. These protective antigens, although identified for *I. scapularis,* may be cross protective between

*Ixodes* species considering the high degree of conservation of gene sequences and protein function between species of the same genus. A 5'-nucleotidase was identified and characterized in *B. microplus* by Liyou et al. (1999; 2000) but they did not assay its protection capacity. Although surprising at first glance, the protection capacity of ribosomal and heat shock protein preparations has been previously documented in other organisms (Elad and Segal, 1995; Silva, 1999; Melby et al., 2000; Cassataro et al., 2002) but never in ticks. The effect of cDNA vaccination on *I. scapularis* experimental infestations of mice was evidenced by the reduction of the number of engorged larvae, the retardation of larval development, the inhibition of molting to nymphal stages and the appearance of visibly damaged larvae with red coloration. These effects were also recorded in vaccination experiments with recombinant BM86 and BM95 against infestations with *B. microplus,* including the red coloration in some ticks, attributed to blood leakage to the tick haemolymph (Garcia-Garcia et al., 2000).

Thus, in one embodiment of the present invention there is provided cDNA sequences, protein encoding fragments thereof, and derived protein sequences for protective *I. scapularis* antigens comprising antigens homologous to endopeptidases, nucleotidases, chorion proteins, vitellogenin receptors, peptidoglycan recognition proteins, glutamine-alanine rich proteins, ribosomal proteins, β-adaptin, Beta-amyloid precursor protein, Block of proliferation (Bop1), lectins, chloride channels, RNA polymerases, ATPases and heat-shock proteins.

In another embodiment of the present invention there is provided a vaccine composition comprising the *I. scapularis* protective recombinant proteins and/or modified cDNAs separately or which may optionally be combined with adjuvant to enhance the protection efficacy of vaccine preparations against *Ixodes* spp., wherein the vaccine composition further comprises a pharmaceutically acceptable carrier or diluent. The vaccine composition also may optionally be combined with tick-borne pathogen components to provide a means to control tick-borne infections, wherein the vaccine composition further comprises a pharmaceutically acceptable carrier or diluent and adjuvant.

In another embodiment of the present invention there is provided a method for inducing an immune response in a mammal to provide immune protection, which reduces or affects infestations by *Ixodes* spp. ticks and/or transmission of tick-borne pathogens, the method comprising administering to at-risk human population and mammalian reservoir an effective amount of a vaccine composition comprising the *I. scapularis* protective recombinant proteins and/or modified cDNAs alone or in combination with an adjuvant or tick-borne pathogen components to provide a means to control tick infestations and to reduce transmission to humans of tick-borne infections, wherein the vaccine composition further comprises a pharmaceutically acceptable carrier or diluent.

A better understanding of the present invention and its objects and advantages will become apparent to those skilled in this art from the following detailed description, wherein there is described only the preferred embodiment of the invention, simply by way of illustration of the best mode contemplated for carrying out the invention. As will be realized, the invention is capable of modifications in various obvious respects, all without departing from the scope and spirit of the invention. Accordingly, the description should be regarded as illustrative in nature and not as restrictive.

DETAILED DESCRIPTION OF THE INVENTION

Before explaining the present invention in detail, it is important to understand that the invention is not limited in its application to the details of the construction illustrated and the steps described herein. The invention is capable of other embodiments and of being practiced or carried out in a variety of ways. It is to be understood that the phraseology and terminology employed herein is for the purpose of description and not of limitation.

The present invention derives from the sequences set forth on the Sequence Listing attached hereto and incorporated herein. In particular, there is provided 25 separate and distinct sequences comprising 14 cloned cDNA molecules and 11 deduced amino acid sequences of encoded polypeptides, said sequences having been isolated and identified as possessing the asserted utility in accordance with the following described experimental methodology.

EXAMPLE 1

Construction of an *I. scapularis* cDNA Library and Screening for Protective Antigens by ELI Tick Cells Monolayers of IDE8 (ATCC CRL 1973) cells, originally derived from embryonic *I. scapularis,* were maintained at 31° C. in L-15B medium supplemented with 5% foetal bovine serum, tryptose phosphate broth and bovine lipoprotein concentrate after Munderloh et al. (1994). Cells were subcultured at 1:5–1:10 when monolayers reached a density of approximately $10^7$ cells/T-25 flask. Medium was replaced weekly.

Library Construction

A cDNA expression library was constructed in the vector pEXP1 containing the strong cytomegalovirus $CMV_{IE}$ promoter (Clontech). Because we planned to target the early larval stages of *I. scapularis,* we chose to construct our library from cultured embryonic *I. scapularis* IDE8 cells-derived poly(A)+ RNA. The cDNA library contained 4.4×

10⁶ independent clones and a titer of approximately $10^{10}$ cfu/ml with more than 93% of the clones with cDNA inserts. The average cDNA size was 1.7 kb (0.5–4.0 kb).

Primary Screen

Figure 1:
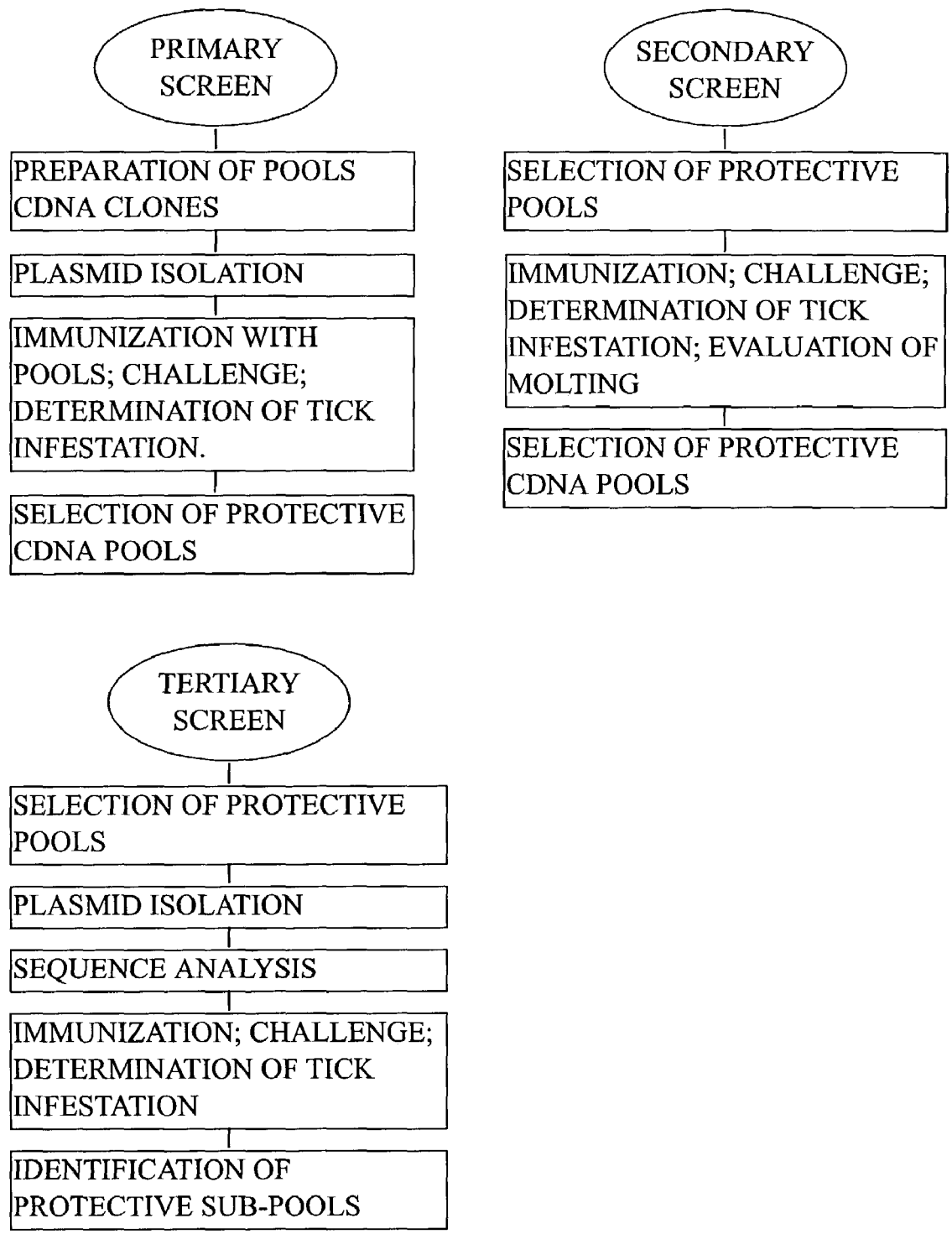
FIG. 1 is a summary of the cDNA ELI approach used to identify protective antigens against *I. scapularis* infestations.

The overall schema for identification of protective antigens through ELI, sequential fractionation and sequence analysis is shown in FIG. 1.

Ninety-six LBA (master) plates containing an average of 41 (30–61) cDNA clones per plate were prepared. Replicas were made and clones from each plate were pooled, inoculated in Luria-Bertani with 50 µg/ml ampicillin, grown for 2 hr in a 96 wells plate and plasmid DNA purified from each pool (Wizard SV 96 plasmid DNA purification system, Promega, Madison, Wis., USA). BALB/c female mice, 5–6 weeks of age at the time of first vaccination, were used. Mice were cared for in accordance with standards set in the Guide for Care and Use of Laboratory Animals. Mice were injected with a 1 ml tuberculin syringe and a 27 gauge needle at days 0 and 14. Three mice per group were each immunized IM in the thigh with 1 µg DNA/dose in 50 µl PBS. Two groups of 3 mice each were included as controls. One group was injected with 1 µg vector DNA alone and the second with saline only. Two weeks after the last immunization, mice were infested with 100 $I.$ $scapularis$ larvae per mouse. Ticks were artificially reared at the Oklahoma State University tick rearing facility by feeding larvae on mice, nymphs on rabbits and adults on sheep and using for infestation in our experiments the larvae obtained from the eggs oviposited by a single female. Twelve hours after tick infestation, larvae that did not attach were counted to calculate the number of attached larvae per mouse and mice were transferred to new cages. Replete larvae dropping from each mouse were collected daily and counted during 7 days. The inhibition of tick infestation (I) for each test group was calculated with respect to vector-immunized controls as $[1-(<RL>n/<RL>c\times<RL>ic/<RL>in)]\times100$, where $<RL>n$ is the average number of replete larvae recovered per mouse for each test group, $<RL>c$ is the average number of replete larvae recovered per mouse for control group, $<RL>ic$ is the average number of larvae attached per mouse for control group, and $<RL>in$ is the average number of larvae attached per mouse for each test group.

Figure 2A:
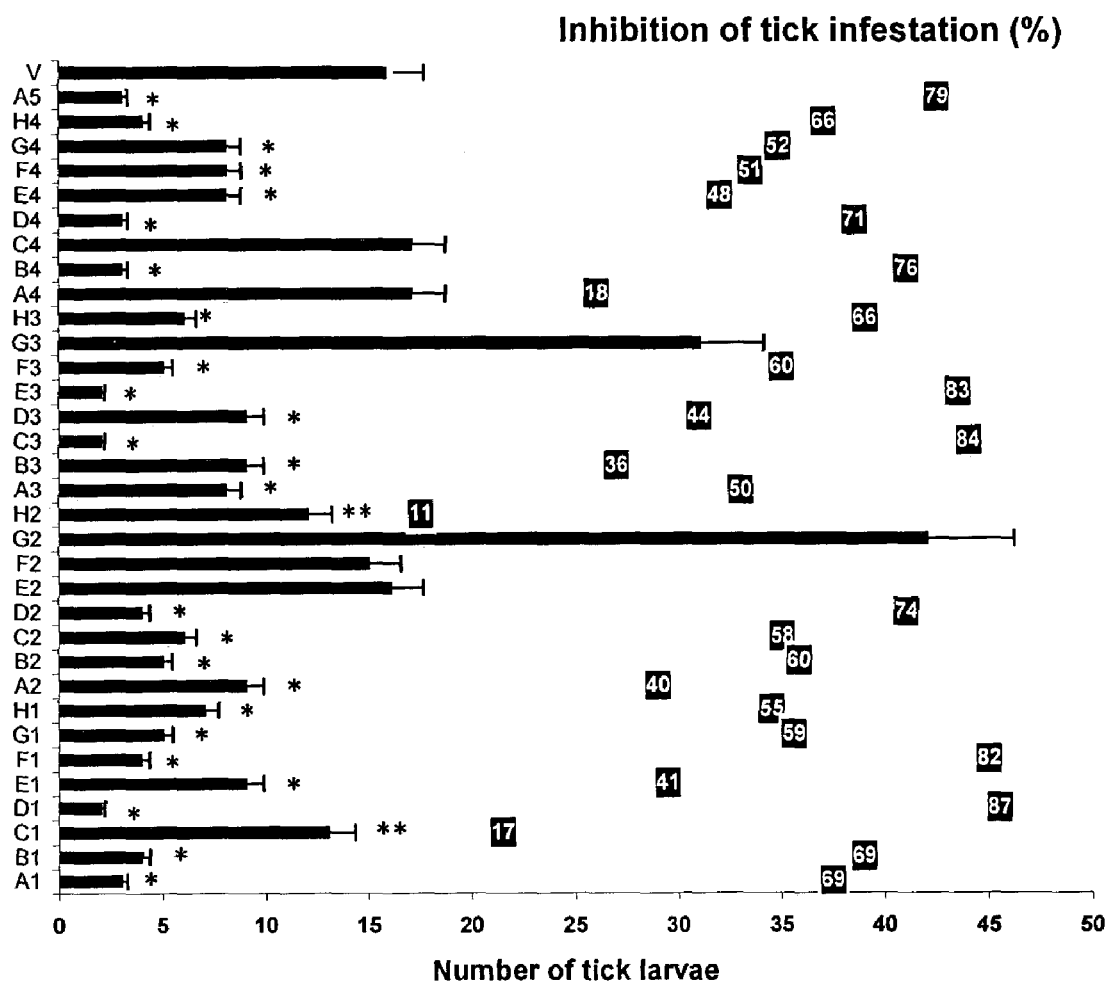
FIG. 2A is a graph depicting the results of a primary screen of cDNA pools (A–H 1–4, A5) by ELI. V, control mice injected with 1 µg vector DNA alone. *$\alpha<0.01$, **$\alpha<0.05$ (Tukey's post-hoc test for pair comparisons after ANOVA). Number in boxes represent values for inhibition of tick infestation with respect to the control group.
Figure 2B:
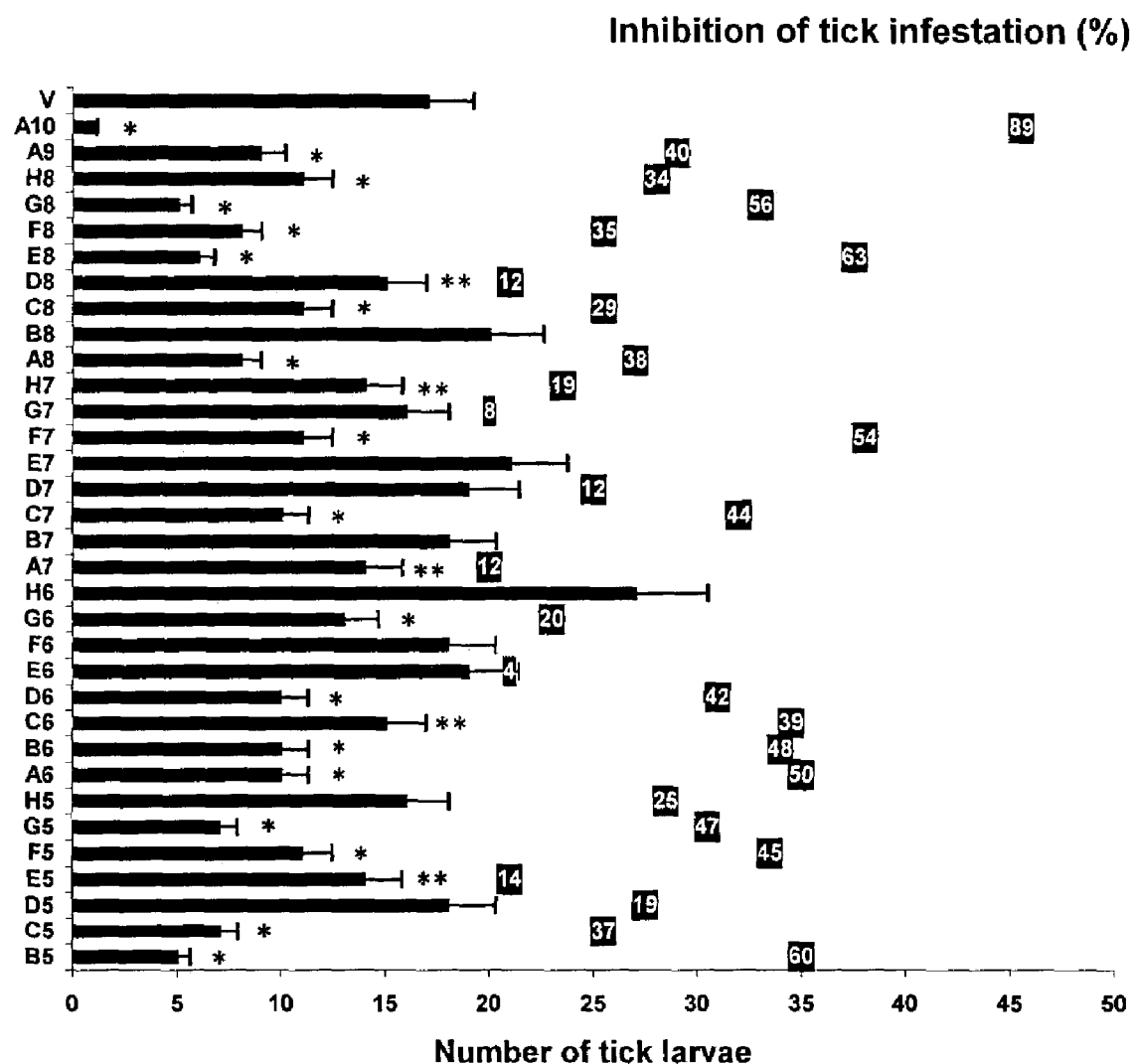
FIG. 2B is a graph depicting the results of a primary screen of cDNA pools (A6–A10, B–H 5–8) by ELI. V, control mice injected with 1 µg vector DNA alone. *$\alpha<0.01$, **$\alpha<0.05$ (Tukey's post-hoc test for pair comparisons after ANOVA). Number in boxes represent values for inhibition of tick infestation with respect to the control group.

Pools of 41 (30–61) $I.$ $scapularis$ cDNA clones were screened by ELI. Only 33 cDNA pools and controls were analyzed per experiment. The average tick infestation level was 50±13 and 56±15 and 56±15 and 54±18 larvae/mouse for cDNA immunized and control mice, respectively (P>0.05) (Table 1). The average number of engorged larvae recovered per mouse was 9±3 and 13±4 in the cDNA-immunized mice and 16±4 and 17±3 in the control vector-immunized group (P<0.05) (Table 1). No reduction was observed in the number of larvae collected from mice that received the vector DNA compared to saline-immunized controls. The maximum number of engorged larvae was collected 3 to 4 days after infestation. However, in mice immunized with cDNA pools B5, A8 and A10 (FIG. 2) a retardation of larval development in 1 to 2 days was recorded. The average inhibition of tick infestation (I) was 49±28% and 30±22% (Table 1). After two experiments covering the analysis of 66 pools (2705 clones), 9 protective pools (351 clones) were selected producing an inhibition of tick infestation I≧60% (FIGS. 2A and 2B and Table 1). When we started these experiments, we planed to screen over 4000 cDNA clones considering the complexity of the tick genome. However, to our surprise 9 protective cDNA pools were identified after screening 66 pools containing 2705 cDNA clones. This result probably reflects the possibility of interfering with tick infestations at many different levels that involve a Pleiades of gene products. Results from vaccination experiments against ticks employing recombinant antigens support this view (reviewed by Mulenga et al., 2000). Because of the complexity of the screening procedure in mice vaccinated and challenged with tick larvae, it was difficult to work with more than 9 protective cDNA pools. Therefore we did not continue screening new cDNA pools and focused our attention on the 9 pools selected after the primary screen.

Secondary Screen

The secondary screen was done to verify the protective capacity of the cDNA pools selected after the primary screen (FIGS. 2A and 2B). After the primary screen of 66 cDNA pools (2705 clones), 9 pools with I≧60% were selected for the secondary screen (re-screening) employing 5 mice per group as described above. Engorged larvae were kept for molting in a 95% humidity atmosphere. Molting of engorged larvae was evaluated by visual examination of tick nymphs under a stereomicroscope 34 days after last larval collection. The inhibition of molting (M) for each test group was calculated with respect to vector-immunized controls as $[1-(MLn/MLc\times RLc/RLn)]\times100$, where MLn is the number of nymphs for each test group, MLc is the number of nymphs for the control group, RLc is the number of larvae recovered for the control group, and RLi is the number of larvae recovered for each test group. Control mice were immunized with the negative (I=0%) F2 cDNA pool or saline only. A group was included immunized SC with two doses of 100 µg of total IDE8 tick cell proteins per dose in Freund's incomplete adjuvant.

All 9 protective cDNA pools gave positive results in the secondary screen (data not shown). The tick infestation levels were higher in this experiment (average 85±6 and 84±3 larvae/mouse for cDNA-immunized and control mice, respectively; P>0.05). Nevertheless, the average number of engorged larvae recovered per mouse was 39±7 and 26±6 for control and cDNA-immunized mice, respectively (P<0.05). The group immunized with total IDE8 tick cell proteins was protected with I=33%. Again, no reduction was observed in the number of larvae collected from mice that received the control cDNA (F2 negative pool after the primary screen; FIG. 2A) compared to saline-immunized controls.

In the secondary screen, molting of engorged larvae was evaluated after 34 days. Molting was affected in all but one test cDNA-immunized group. Inhibition of molting in test cDNA-immunized mice compared to the control cDNA-immunized group varied from 0% to 12% (6±4%). The inhibition of molting was higher than 50% only in the larvae collected from mice immunized with cDNA pools B5 and A10, which showed a retardation of larval development in 1 to 2 days as in the primary screen. No differences were observed between control cDNA and saline-immunized mice. Among the larvae that did not molt to nymph, some were visibly damaged and presented a strong red coloration. The percent of red larvae in cDNA-immunized mice varied between 3% to 18% (7±5%) while in the saline and control cDNA-immunized groups red larvae represented the 6% and 4%, respectively.

Tertiary Screen

For the tertiary screen, 64 clones were grouped in 16 sub-pools each containing 1 to 17 plasmids according to the predicted function of encoded proteins (e.g., all the plasmids that encoded histone proteins were grouped together) and used with 4 sub-pools containing 182 clones of unknown function or with sequences without homology to sequence databases to immunize 4 mice per group. Mice were immunized with 0.3 µg/plasmid/dose in 50 µl PBS and evaluated as described above. Control mice were immunized with a pool of 20 plasmids containing mitochondrial cDNAs.

Figure 3:
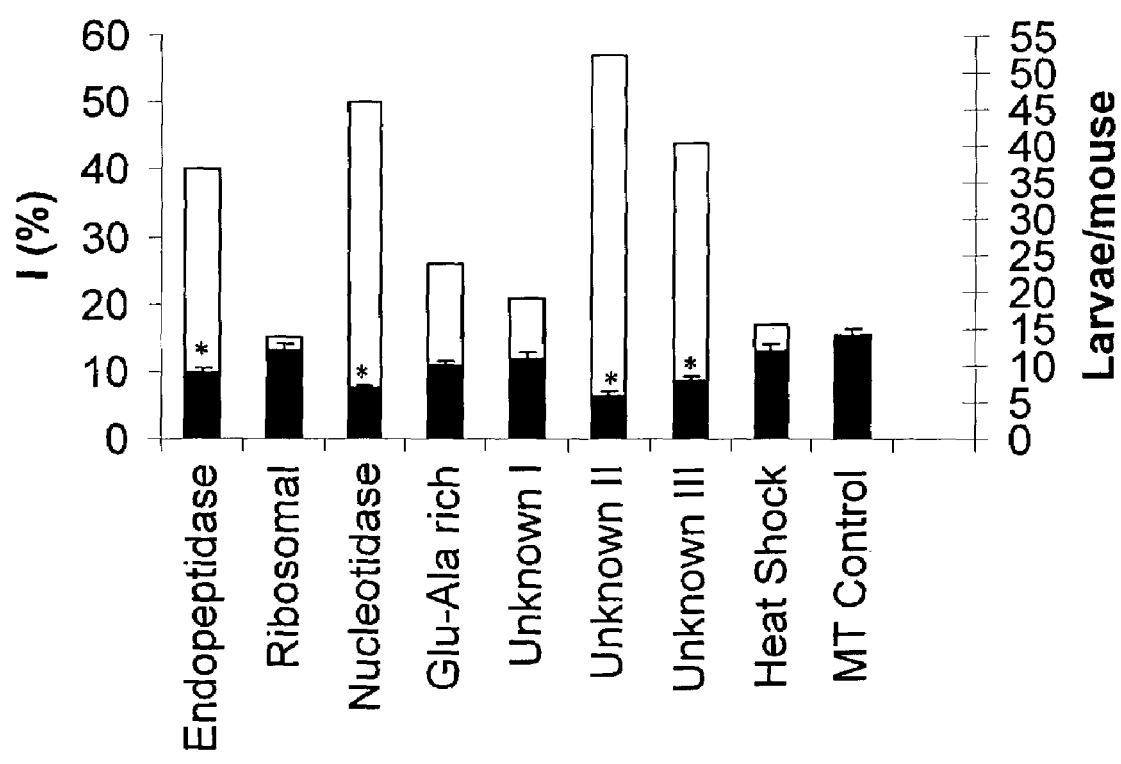
FIG. 3 is a graph depicting the results of a tertiary screen by ELI of cDNA sub-pools formed according to the predicted function of encoded proteins. Only groups with I≧15% are shown (white bars). The number of engorged larvae per mouse is expressed as mean±SD (black bars). Control mice were injected with mitochondrial (MT) cDNAs. *$P \leq 0.05$ (Student's t-test).

Tick infestation levels were similar in all test groups (72±2 larvae/mouse) and in control mice (69±2 larvae/mouse) ($P>0.05$). The number of engorged larvae recovered per mouse was also similar between test (16±7) and control (14±6) mice ($P>0.05$). However, the groups immunized with cDNA sub-pools containing clones with putative endopeptidase, nucleotidase, ribosomal proteins, heat shock proteins, glutamine-alanine-rich proteins and 3 of the sub-pools with unknown function or with sequences without homology to sequence databases had $I \geq 15\%$ (FIG. 3). Furthermore, among them, the groups immunized with sub-pools containing clones with a putative endopeptidase, nucleotidase and two of the cDNA sub-pools with unknown function or with sequences without homology to sequence databases resulted in lower infestation levels compared to control mice ($P \leq 0.05$) and $I \geq 40\%$ (FIG. 3). Clones homologous to chorion proteins, vitellogenin receptors, and peptidoglycan recognition proteins were selected for they potential protection capacity in other stages of tick development.

Statistical Analysis

The number of larvae attached per mouse and the number of engorged larvae recovered per mouse 7 days after infestation were compared by Analysis of Variance (ANOVA) followed by a series of Tukey's post-hoc tests for pair comparisons between cDNA-immunized and control vector DNA-immunized mice (primary screen), and by Student's t-test between mice immunized with positive cDNA pools and the control negative F2 cDNA pool (secondary screen) or between test cDNA sub-pools-immunized and control mice immunized with mitochondrial cDNAs (tertiary screen).

EXAMPLE 2

Sequence Analysis of Protective Clones

All the 351 cDNA clones in the 9 pools that resulted positive in the secondary screen were sequenced. DNA from individual clones in these pools was purified (Wizard SV 96 plasmid DNA purification system, Promega) from the master plate and partially sequenced. In most cases a sequence larger than 700 nucleotides was obtained. Nucleotide sequences were analyzed using the program AlignX (Vector NTI Suite V 5.5, InforMax, North Bethesda, Md., USA). BLAST (Altschul et al., 1990) was used to search the NCBI databases to identify previously cloned sequences that may have homology to those that we sequenced. Sequence analysis allowed grouping the clones according to sequence identity to DNA databases and predicted protein function. The protective clones selected after the tertiary screen were fully sequenced.

Comparison to sequence databases permitted to identify sequence identity to previously reported genes with known function in 152 (43%) of the clones (Table 2). Fifty seven percent of the sequences were homologous to genes with unknown function or had no significant identity to previously reported sequences (Table 2). Of the clones with sequence identity to genes with known function, 85% were homologous to arthropod sequences. Ninety-three clones (61%) contained sequences homologous to *Drosophila melanogaster*, 5 (3%) to other insects and 32 (21%) to Ixodid tick species. Thirty percent of the clones were eliminated from further analysis based on their sequence identity, including those containing similar sequences (Table 2). The protective clones included antigens homologous to endopeptidases, nucleotidases, chorion proteins, vitellogenin receptors, peptidoglycan recognition proteins, glutamine-alanine rich proteins, ribosomal proteins, and heat-shock proteins.

SUMMARY OF RESULTS

The results obtained with the various protective clones identified in the Sequence Listing, along with certain selected expressed proteins, are summarized in Table 4.

SEQ ID NO:1 denotes the clone designated 4E6, wherein the relevant protein encoding fragment has been identified as comprising residues 1–117, which encodes the polypeptide shown in SEQ ID NO: 2.

SEQ ID NO:3 denotes the clone designated 4D8, wherein the relevant protein encoding fragment has been identified as comprising residues 80–575, which encodes the polypeptide shown in SEQ ID NO: 4.

SEQ ID NO:5 denotes the clone designated 4F8, wherein the relevant protein encoding fragment has been identified as comprising residues 1–951, which encodes the polypeptide shown in SEQ ID NO: 6.

SEQ ID NO:7 denotes the clone designated 4G11, wherein the relevant protein encoding fragment has been identified as comprising residues 1–697, which encodes the polypeptide shown in SEQ ID NO: 8.

SEQ ID NO:9 denotes the clone designated 4D6, wherein the relevant protein encoding fragment has been identified as comprising residues 198–1025, which encodes the polypeptide shown in SEQ ID NO: 10.

SEQ ID NO:11 denotes the clone designated 3E1, wherein the relevant protein encoding fragment has been identified as comprising residues 3–578, which encodes the polypeptide shown in SEQ ID NO: 12.

SEQ ID NO:13 denotes the clone designated 1C10, wherein the relevant protein encoding fragment has been identified as comprising residues 1–1119, which encodes the polypeptide shown in SEQ ID NO: 14.

SEQ ID NO:15 denotes the clone designated 3E10, wherein the relevant protein encoding fragment has been identified as comprising residues 51–1544, which encodes the polypeptide shown in SEQ ID NO: 16.

SEQ ID NO:17 denotes the clone designated 4F11, wherein the relevant protein encoding fragment has been identified as comprising residues 31–2295, which encodes the polypeptide shown in SEQ ID NO: 18.

SEQ ID NO:19 denotes the clone designated 3C12, wherein the relevant protein encoding fragment has been identified as comprising residues 6–332, which encodes the polypeptide shown in SEQ ID NO: 20.

SEQ ID NO:21 denotes the clone designated 2C12, wherein the relevant protein encoding fragment has been identified as comprising residues 3–137, which encodes the polypeptide shown in SEQ ID NO: 22.

SEQ ID NOS: 22, 23 AND 24, denote, respectively, clones 1A9, 1B2 and 4A4, each comprising a partial sequence with no associated polypeptide.

\* \* \* \* \*

As noted above, the present invention relates to the sequences identified in the Sequence Listing. More generally, the invention concerns the given cDNA sequences and any nucleotide sequence coding for a protein which is capable of eliciting an antibody or other immune response (e.g., T-cell response of the immune system) which recognizes an epitope(s) of the amino acid sequences depicted in the Sequence Listing, including less than the full cDNA sequences and mutants thereof. Hence the nucleotide sequence may encode a protein which is the entire antigen encoded by the variously identified bases, or a fragment or derivative of the antigen or a fusion product of the antigen or fragment and another protein, provided that the protein which is produced from such sequence is capable of eliciting an antibody or other immune response which recognizes an epitope(s) of the given amino acid sequences.

As a result, the invention encompasses DNA sequences which encode for and/or express in appropriate transformed cells, proteins which may be the full length antigen, antigen fragment, antigen derivative or a fusion product of such antigen, antigen fragment or antigen derivative with another protein.

Proteins included within the present invention have an amino acid sequence depicted in the Sequence Listing. Other included proteins consist of a fragment of said sequence capable of eliciting an antibody or other immune response which recognizes an epitope(s) of the amino acid sequences depicted and a mutuant of said sequence capable of eliciting an antibody or other immune response which recognizes an epitope(s) of such amino acid sequences.

The nucleotide sequences may be inserted into any of a wide variety of expression vectors by a variety of procedures. Such procedures and others are deemed to be known by those skilled in the art. Suitable vectors include chromosomal, nonchromosomal and synthetic DNA sequences; e.g., derivatives of SV40; bacterial plasmids; phage DNAs; yeast plasmids; vectors derived from combinations of plasmids and phage DNAs, viral DNA such as baculovirus, vaccinia, adenovirus, fowl pox virus, pseudorabies, etc. The appropriate DNA sequence must be operatively linked in the vector to an appropriate expression control sequence(s) (promoter) to direct mRNA synthesis. As representative examples of such promoters, there may be mentioned LTR or SV40 promoter, the *E. coli* lac or trp, the phage lambda PL promoter and other promoters known to control expression of genes in prokaryotic and eukaryotic cells or their viruses. The expression vector also includes a non-coding sequence for a ribosome binding site for translation initiation and a transcription terminator. The vector may also include appropriate sequences for amplifying expression.

The vector containing the appropriate cDNA sequence as hereinabove described, as well as an appropriate promoter or control sequence, may be employed to transform an appropriate host to permit the host to express the protein. Examples of host organisms and cells include bacterial strains (e.g., *E. coli, Pseudomonas, Bacillus, Salmonella*, etc.), fungi (e.g., yeasts and other fungi), animal or plant hosts (e.g., mouse, swine or animal and human tissue cells). The selection of the host is deemed to be within the scope of those skilled in the art.

It is also understood that the appropriate cDNA sequence present in the vector when introduced into a host may express part or only a portion of the protein which is encoded within the noted terminology, it being sufficient that the expressed protein be capable of eliciting an antibody or other immune response which recognizes an epitope(s) of the listed amino acid sequences.

The isolated cDNAs and/or polypeptide expressed by the host transformed by the vector may be harvested by methods which will occur to those skilled in the art and used in a vaccine for protection of a mammal, such as a bovine, swine, human, etc., against infestations of *Ixodes* species. Such protective recombinant proteins and/or modified cDNAs are used in an amount effective to induce an immune response against *Ixodes* species ticks and their associated pathogens and may be used in combination with a suitable physiologically acceptable carrier. The term "inducing an immune response" when used with respect to the vaccine described herein means that the vaccine prevents disease associated with a particular tick species or reduces the severity of the disease.

The carrier employed in conjunction with vaccine may be any one of a wide variety of carriers. As representative examples of suitable carriers, there may be mentioned mineral oil, synthetic polymers, etc. Carriers for vaccines are well known in the art and the selection of a suitable carrier is deemed to be within the scope of those skilled in the art. The selection of a suitable carrier is also dependent upon the manner in which the vaccine is to be administered.

The present invention provides a method of immunizing a susceptible mammal, against infestations and disease caused by *Ixodes* species with the vaccine described above. For purposes of this invention, the vaccine is administered in an effective amount. The vaccine may be administered by any of the methods well known to those skilled in the art, for example, by intramuscular, subcutaneous, intraperitoneal or intravenous injection. Alternatively, the vaccine may be administered intranasally or orally. It is also to be understood that the vaccine may include active components, such as tick-borne pathogen components or adjuvants in addition to the antigen(s) or fragments hereinabove described.

The host expressing the antigen may itself be used to deliver antigen to non-human animals, by introducing killed or viable host cells that are capable of propagating in the animal. Direct incorporation of the cDNA sequences into host cells may also be used to introduce the sequences into animal cells for expression of antigen in vivo.

BIBLIOGRAPHY

The following references are incorporated herein by reference:

Alberti E, Acosta A, Sarmiento M E, Hidalgo C, Vidal T, Fachado A, Fonte L, Izquierdo L, Infante J F, Finlay C M, Sierra G. Specific cellular and humoral immune response in Balb/c mice immunised with an expression genomic library of *Trypanosoma cruzi*. Vaccine 1998; 16: 608–12.

Altschul S F, Gish W, Miller W, Myers E W, Lipman D J. Basic local alignment search tool. J Mol Biol 1990; 215: 403–10.

Barry M A, Lai W C, Johnston S A. Protection against mycoplasma infection using expression-library immunization. Nature 1995; 377: 632–5.

Black W C 4th, Piesman J. Phylogeny of hard- and soft-tick taxa (Acari: Ixodida) based on mitochondrial 16S rDNA sequences. Proc Natl Acad Sci USA 1994; 91: 10034–8.

Brayton K A, Vogel S W, Allsopp B A. Expression library immunization to identify protective antigens from *Cowdria ruminantium*. Ann N Y Acad Sci 1998; 849: 369–71.

Cassataro J, Velikovsky C A, Giambartolomei G H, Estein S, Bruno L, Cloeckaert A, Bowden R A, Spitz M, Fossati C A. Immunogenicity of the *Brucella melitensis* recombinant ribosome recycling factor-homologous protein and its cDNA. Vaccine 2002; 20: 1660–9.

de la Fuente J, Rodriguez M, Redondo M, Montero C, Garcia-Garcia J C, Mendez L, Serrano E, Valdes M, Enriquez A, Canales M, Ramos E, Boue O, Machado H, Lleonart R, de Armas C A, Rey S, Rodriguez J L, Artiles M, Garcia L. Field studies and cost-effectiveness analysis of vaccination with Gavac against the cattle tick *Boophilus microplus*. Vaccine 1998; 16: 366–73.

de la Fuente J, Rodriguez M, Montero C, Redondo M, Garcia-Garcia J C, Mendez L, Serrano E, Valdes M, Enriquez A, Canales M, Ramos E, Boue O, Machado H, Lleonart R. Vaccination against ticks (*Boophilus* spp.): the experience with the Bm86-based vaccine Gavac. Genet Anal 1999; 15: 143–8.

de la Fuente J, Rodriguez M, Garcia-Garcia J C. Immunological control of ticks through vaccination with *Boophilus microplus* gut antigens. Ann N Y Acad Sci 2000; 916: 617–21.

De Rose R, McKenna R V, Cobon G, Tennent J, Zakrzewski H, Gale K, Wood P R, Scheerlinck J P, Willadsen P. Bm86 antigen induces a protective immune response against *Boophilus microplus* following DNA and protein vaccination in sheep. Vet Immunol Immunopathol 1999; 71: 151–60.

de Vos S, Zeinstra L, Taoufik O, Willadsen P, Jongejan F. Evidence for the utility of the Bm86 antigen from *Boophilus microplus* in vaccination against other tick species. Exp Appl Acarol 2001; 25: 245–61.

Drew D R, Lightowlers M, Strugnell R A. Vaccination with plasmid DNA expressing antigen from genomic or cDNA gene forms induces equivalent humoral immune responses. Vaccine 1999; 18: 692–702.

Elad D, Segal E. Immunogenicity in calves of a crude ribosomal fraction of *Trichophyton verrucosum*: a field trial. Vaccine 1995; 13: 83–7.

Estrada-Peña A, Jongejan F. Ticks feeding on humans: a review of records on human-biting Ixodoidea with special reference to pathogen transmission. Exp Appl Acarol 1999; 23: 685–715.

Garcia-Garcia J C, Gonzalez I L, Gonzalez D M, Valdes M, Mendez L, Lamberti J, D'Agostino B, Citroni D, Fragoso H, Ortiz M, Rodriguez M, de la Fuente J. Sequence variations in the *Boophilus microplus* Bm86 locus and implications for immunoprotection in cattle vaccinated with this antigen. Exp Appl Acarol 1999; 23: 883–95.

Kofta W, Wedrychowicz H. c-DNA vaccination against parasitic infections: advantages and disadvantages. Vet Parasitol 2001; 100: 3–12.

Liyou N, Hamilton S, Elvin C, Willadsen P. Cloning and expression of ecto 5'-nucleotidase from the cattle tick *Boophilus microplus*. Insect Mol Biol 1999; 8: 257–66.

Liyou N, Hamilton S, Mckenna R, Elvin C, Willadsen P. Localization and functional studies on the 5'-nucleotidase of the cattle tick *Boophilus microplus*. Exp Appl Acarol 2000; 24: 235–46.

Manoutcharian K, Terrazas L I, Gevorkian G, Govezensky T. Protection against murine cysticercosis using cDNA expression library immunization. Immunol Lett 1998; 62: 131–6.

Melby P C, Ogden G B, Flores H A, Zhao W, Geldmacher C, Biediger N M, Ahuja S K, Uranga J, Melendez M. Identification of vaccine candidates for experimental visceral leishmaniasis by immunization with sequential fractions of a cDNA expression library. Infect Immun 2000; 68: 5595–602.

Moore R J, Lenghaus C, Sheedy S A, Doran T J. Improved vectors for expression library immunization—application to *Mycoplasma hyopneumoniae* infection in pigs. Vaccine 2001; 20: 115–20.

Mulenga A, Sugimoto C, Onuma M. Issues in tick vaccine development: identification and characterization of potential candidate vaccine antigens. Microbes Infect 2000; 2: 1353–61.

Munderloh U G, Wang Y L M, Chen C, Kurtti T J. Establishment, maintenance and description of cell lines from the tick *Ixodes scapularis*. J Parasitol 1994; 80: 533–43.

Nuttall P A. Pathogen-tick-host interactions: *Borrelia burgdorferi* and TBE virus. Zentralbl Bakteriol 1999; 289: 492–505.

Parola P, Raoult D. Tick-borne bacterial diseases emerging in Europe. Clin Microbiol Infect 2001; 7: 80–3.

Silva C L. The potential use of heat-shock proteins to vaccinate against mycobacterial infections. Microbes and Infection 1999; 1: 429–35.

Singh R A, Wu L, Barry M A. Generation of genome-wide CD8 T cell responses in HLA-A*0201 transgenic mice by an HIV-1 ubiquitin expression library immunization vaccine. J Immunol 2002; 168: 379–91.

Smooker P M, Setiady Y Y, Rainczuk A, Spithill T W. Expression library immunization protects mice against a challenge with virulent rodent malaria. Vaccine 2000; 18: 2533–40.

van Drunen Littel-van den Hurk S, Loehr B I, Babiuk L A. Immunization of livestock with DNA vaccines: current studies and future prospects. Vaccine 2001; 19: 2474–9.

Wikel S K, Ramachandra R N, Bergman D K, Burkot T R, Piesman J. Infestation with pathogen-free nymphs of the tick *Ixodes scapularis* induces host resistance to transmission of *Borrelia burgdorferi* by ticks. Infect Immun 1997; 65: 335–8.Willadsen P. Novel vaccines for ectoparasites. Vet Parasitol 1997; 71: 209–22.

Willadsen P, Jongejan F. Immunology of the tick-host interaction and the control of ticks and tick-borne diseases. Parasitol Today 1999; 15: 258–62.

TABLE 1

Primary screen of the *I. scapularis* cDNA library by ELI in mice.

| Experimental group[a] | Number of pools screened (Number of clones) | Average ± SD number of larvae attached per mouse[b] | Average ± SD number of engorged larvae per mouse[c] | Average ± SD inhibition of tick infestation (I)[d] | Number of pools selected for the secondary screen |
|---|---|---|---|---|---|
| Experiment 1 | 33 (1383) | 50 ± 13 (33–80) | 9 ± 3 (2–42) | 39 ± 55% (−183–87%) | 6 (I > 75%) |
| Vector DNA-immunized controls for experiment 1 | — | 56 ± 13 (45–67) | 16 ± 4 (5–27) | — | — |
| Experiment 2 | 33 (1322) | 56 ± 15 (29–79) | 13 ± 4 (1–27) | 27 ± 28% (−53– 89%) | 3 (I > 60%) |

TABLE 1-continued

Primary screen of the *I. scapularis* cDNA library by ELI in mice.

| Experimental group[a] | Number of pools screened (Number of clones) | Average ± SD number of larvae attached per mouse[b] | Average ± SD number of engorged larvae per mouse[c] | Average ± SD inhibition of tick infestation (I)[d] | Number of pools selected for the secondary screen |
|---|---|---|---|---|---|
| Vector DNA-immunized controls for experiment 2 | — | 54 ± 18 (36–73) | 17 ± 3 (6–28) | — | — |

[a]Ninety six LBA plates containing an average of 41 cDNA clones per plate were prepared. Replicas were made and clones from each plate were pooled, inoculated, grown for 2 hr in a 96 wells plate and plasmid DNA purified from each pool for ELI. Three mice per group were each immunized IM twice with 1 μg DNA/dose in 50 μl PBS two weeks apart. Two groups of 3 mice each were included as controls. One group was injected with vector DNA and the second with saline only.
[b]Fifteen days after the last immunization, mice were infested with 100 *I. scapularis* larvae per mouse. Twelve hrs later, larvae that did not attach were counted to calculate the number of attached larvae per mouse and mice were transferred to new cages.
[c]Engorged larvae dropping from each mouse were collected daily and counted after 7 days.
[d]The inhibition of tick infestation (I) for each test group was calculated with respect to vector-immunized controls as [1-(RLn/RLc × RLic/RLin)] × 100, where RLn is the average number of replete larvae recovered per mouse for each test group, RLc is the average number of replete larvae recovered per mouse for control group, RLic is the average number of larvae attached per mouse for control group, and RLin is the average number of larvae attached per mouse for eachtest group.

TABLE 2

Classification of the clones in protective pools by putative protein function according to identity to sequence databases.

| Putative protein Function | Number of clones |
|---|---|
| Biosynthetic[a] | 2 |
| Catabolism | 4 |
| Cell adhesion | 2 |
| Cell cycle[a] | 2 |
| Cytoskeletal[a] | 8 |
| Defense | 2 |
| DNA structure or replication[a] | 3 |
| Extracellular matrix | 3 |
| Endocytosis | 2 |
| Energy metabolism | 10 |
| Homeostasis | 2 |
| Morphogenetic | 9 |
| Mitochondrial[a] | 34 |
| Protein synthesis or processing[a,b] | 34 |
| RNA synthesis or processing[a] | 7 |
| Heat-shock proteins | 4 |
| Signal transduction | 16 |
| Transport | 8 |
| Unknown | 199 |
| Total | 351 |

[a]Eliminated from further screening of protective antigens. Other clones were eliminated for containing similar sequences.
[b]Except for ribosomal proteins.

TABLE 3

Grouping of the clones according to the predicted function of encoded proteins in sub-pools for the tertiary screen.

| Sub-pool (No. of clones) | Clone | Pool[a] |
|---|---|---|
| Ribosomal (17) | 1A2, 1A10, 1C11 | A5 |
| | 1F6 | D1 |
| | 2B8 | A10 |
| | 2F8, 2F10 | E8 |
| | 3A10, 2C3, 3D2, 3D10 | B4 |
| | 3G9, 3G10 | E3 |
| | 4D11, 4D12, 4E7, 4F7 | F1 |
| Membrane protein (7) | 1D8, 1D11, 1E10 | D1 |
| | 2B12 | A10 |
| | 2H5 | E8 |
| | 3C9 | B4 |
| | 3G11 | E3 |
| ATPase (6) | 1A9, 1B2, 1C9 | A5 |
| | 2C9 | A10 |
| | 4A4 | C3 |
| | 4G12 | F1 |
| Cell channel/Transporter (5) | 1F4 | D1 |
| | 2H11 | E8 |
| | 4A12 | C3 |
| | 4G10, 4G11 | F1 |
| Early development-specific (4) | 1C8 | A5 |
| | 3F4 | E3 |
| | 4C7 | C3 |
| | 4G9 | F1 |
| G protein-coupled receptor (4) | 2B7, 2C12 | A10 |
| | 2F12 | E8 |
| | 4C9 | C3 |
| Growth factor receptor (3) | 2E8 | B5 |
| | 3B8, 3C8 | B4 |
| Lectin (3) | 3E10 | E3 |
| | 4B8, 4C8 | C3 |
| Vitellogenin (3) | 1F12 | D1 |
| | 4A6 | C3 |
| | 4G2 | F1 |
| Heat shock (3) | 1C10 | A5 |
| | 1F10 | D1 |
| | 3F6 | E3 |
| EGF-like (2) | 2H4 | E8 |
| | 4C10 | C3 |
| Secreted protein (2) | 2F9 | E8 |
| | 3C12 | B4 |
| Glutamine-Alanine rich (2) | 4D6, 4E6 | F1 |
| Adaptin (1) | 3E1 | E3 |

TABLE 3-continued

Grouping of the clones according to the predicted function of encoded proteins in sub-pools for the tertiary screen.

| Sub-pool (No. of clones) | Clone | Pool[a] |
|---|---|---|
| Endopeptidase (1) | 4D8 | F1 |
| Nucleotidase (1) | 4F8 | F1 |

[a]cDNA pools refer to positive pools after primary and secondary screens (FIG. 2A and 2B).

TABLE 4

Summary of results with *I. scapularis* cDNA clones.

| cDNA clone | Predicted Protein | Inhibition of tick infestation I (%) | Inhibition of molting M % | Efficacy E (%) |
|---|---|---|---|---|
| 4D8 | Endopeptidase | 40*/54** | 7*/8** | 44*/58** |
| 4F8 | Nucleotidase | 50*/64** | 17*/−9** | 58*/61** |
| 1C10 | HSP70 | 17* | ND | ND |
| 4D6 | Glu-Ala-rich | 61* | 11 | 66* |
| 4E6 | Glu-Ala-rich | 20*/46** | 16** | 55** |
| 3E1 | β-adaptin (appendage region) | 27* | 5* | 31* |
| 2C12 | Beta-amyloid precursor protein (APP) | −8*** | ND | ND |
| 4F11 | Block of proliferation Bop1 | −39*** | ND | ND |
| 3E10 | Mannose binding lectin | −48*/−10*** | ND | ND |
| 4G11 | Chloride channel | 38*** | 30 | 57 |
| 3C12 | RNA polymerase III | −104*** | ND | ND |
| 1A9, 1B2, 4A4 | ATPase | −57*** | ND | ND |

Mice were immunized with cDNA-containing expression plasmid DNA as described above (*) or with 100 μg/dose of recombinant protein expressed in *E. coli* (**). I, M and E were calculated as described above. ND, not determined.
***Resulted in a pro-feeding activity. This effect could be due to the expression of cDNAs encoding for tick immunosuppressants, anticoagulants and other proteins with low antigenicity and a pro-feeding activity. Alternatively, they could encode for proteins homologous to host proteins with anti-tick activity, which neutralization results in a tick pro-feeding activity.

In view of the above, it will be seen that the several objectives of the invention are achieved and other advantageous results attained. As various changes could be made in the above DNA molecules, proteins, etc. without departing from the scope of the invention, it is intended that all matter contained in the above description or shown in the accompanying drawings shall be interpreted as illustrative and not in a limiting sense. While the invention has been described with a certain degree of particularity, it is understood that the invention is not limited to the embodiment(s) set for herein for purposes of exemplification, but is to be limited only by the scope of the attached claim or claims, including the full range of equivalency to which each element thereof is entitled.

What is claimed is:

1. An isolated cDNA molecule which encodes an *Ixodes* associated antigenic polypeptide, said molecule having a nucleoxide sequence comprising at least residues 80-575 of SEQ ID NO: 3.

2. An expression vector comprising the isolated cDNA molecule of claim 1.

3. An isolated cell transformed by the expression vector of claim 2.

4. The isolated cDNA molecule of claim 1, wherein said cDNA molecule encodes a polypeptide represented by SEQ ID NO: 4.

5. The isolated cDNA molecule of claim 1, wherein said cDNA molecule encodes a polypeptide that induces antibodies specific for an amino acid sequence represented by SEQ ID NO: 4.

* * * * *